US011471611B2

(12) United States Patent
Wilke et al.

(10) Patent No.: US 11,471,611 B2
(45) Date of Patent: Oct. 18, 2022

(54) MULTI-COMPONENT SAFETY NEEDLE COVER

(71) Applicant: APIJECT LIMITED, Uckfield (GB)

(72) Inventors: Tobias Wilke, Uckfield (GB); Bernd Mohr, Uckfield (GB)

(73) Assignees: Tobias Wilke, Ibbenbuehren (DE); Bernd Mohr, Bramstedt (DE); Stephan Fischer, Hiddenhausen (DE)

( * ) Notice: Subject to any disclaimer, the term of this patent is extended or adjusted under 35 U.S.C. 154(b) by 169 days.

(21) Appl. No.: 16/787,279

(22) Filed: Feb. 11, 2020

(65) Prior Publication Data

US 2020/0246553 A1 Aug. 6, 2020

Related U.S. Application Data

(63) Continuation of application No. PCT/IB2018/000389, filed on Mar. 23, 2018.
(Continued)

(51) Int. Cl.
*A61M 5/32* (2006.01)
*A61M 5/315* (2006.01)
(Continued)

(52) U.S. Cl.
CPC ...... *A61M 5/3202* (2013.01); *A61M 5/31528* (2013.01); *A61M 5/321* (2013.01); *A61M 5/348* (2013.01); *A61M 5/3216* (2013.01); *A61M 5/50* (2013.01); *A61M 5/5086* (2013.01); *A61M 2005/3217* (2013.01)

(58) Field of Classification Search
CPC .... A61M 5/50; A61M 5/3216; A61M 5/3213; A61M 5/1626; A61M 5/5086;
(Continued)

(56) References Cited

U.S. PATENT DOCUMENTS 4,838,871 A * 6/1989 Luther ............... A61M 5/3216
604/263
5,405,332 A * 4/1995 Opalek ............... A61M 5/3216
604/263
(Continued)

FOREIGN PATENT DOCUMENTS

EP 0724890 8/1996
GB 2277032 A 10/1994

*Primary Examiner* — Rebecca E Eisenberg
*Assistant Examiner* — Anna E Goldberg-Richmeier
(74) *Attorney, Agent, or Firm* — Von Rohrscheidt Patents

(57) ABSTRACT

A safety cover configured to be coupled to an injection device and to provide a protective enclosure for a needle of the injection device, the safety cover including an outer cover member; an inner cover member coupled to the outer cover member in a concentric arrangement so that the outer cover member encloses at least a portion of the inner cover member, wherein the outer cover member is configured to move relative to the inner cover member from an unlocked position, in which the needle of the injection device is accessible for use, to a locked position, in which the outer cover member and the inner cover member are fixed at one another and the needle of the injection device is inaccessible, wherein the outer cover member includes a body that includes a proximal end, a distal end, and a cavity defined within the body.

16 Claims, 32 Drawing Sheets

Related U.S. Application Data

(60) Provisional application No. 62/646,700, filed on Mar. 22, 2018, provisional application No. 62/501,127, filed on May 4, 2017, provisional application No. 62/477,419, filed on Mar. 27, 2017, provisional application No. 62/476,722, filed on Mar. 24, 2017.

(51) Int. Cl.
*A61M 5/34* (2006.01)
*A61M 5/50* (2006.01)

(58) Field of Classification Search
CPC .... A61M 5/321; A61M 5/3202; A61M 5/348; A61M 2005/3217
See application file for complete search history.

(56) References Cited

U.S. PATENT DOCUMENTS

| | | | |
|---|---|---|---|
| 7,771,397 B1* | 8/2010 | Olson | A61M 5/3202 |
| | | | 604/263 |
| 2003/0036732 A1* | 2/2003 | Marano-Ford | A61M 5/3216 |
| | | | 604/199 |
| 2003/0181868 A1* | 9/2003 | Swenson | A61B 5/150717 |
| | | | 604/263 |
| 2011/0282296 A1 | 11/2011 | Harms | |
| 2012/0029441 A1* | 2/2012 | Madin | A61M 5/3216 |
| | | | 604/192 |
| 2012/0210569 A1* | 8/2012 | Schmitt | A61M 25/09041 |
| | | | 29/700 |
| 2018/0140780 A1* | 5/2018 | Carrel | A61M 5/3216 |

* cited by examiner

MULTI-COMPONENT SAFETY NEEDLE COVER

RELATED APPLICATIONS

This application is a continuation of International application PCT/IB2018/000389 filed on Mar. 23, 2018, This application claims the benefit of, and priority to, U.S. Provisional Application No. 62/476,722, filed Mar. 24, 2017, U.S. Provisional Application No. 62/477,419, filed Mar. 27, 2017, U.S. Provisional Application No. 62/501,127, filed May 4, 2017, and U.S. Provisional Application No. 62/646,700, filed Mar. 22, 2018, the contents of each of which are hereby incorporated by reference herein in their entireties.

FIELD OF THE INVENTION

The present invention generally relates to safety devices, and, more particularly, to a multi-component safety needle cover for use with injection devices, such as syringes, wherein the safety needle cover is configured to prevent needlestick injury by permanently covering the needle after use thereof.

BACKGROUND OF THE INVENTION

As those within the medical field have developed an understanding that a variety of diseases may be transferred via unclean and previously used needles, a wide variety of devices have been developed for protecting medical practitioners and other individuals from previously utilized needles. A needlestick injury generally occurs in a medical environment, and particularly before or after use of a syringe or other injection device, when the user accidentally sticks the needle into himself or herself, or another person. It is important to prevent such injuries, since they can spread infections and diseases.

There are several known devices and systems for reducing the risk of needlestick. For example, some syringes are made with needles configured to be retracted automatically after use by means of a spring within the syringe. However, this type of safety syringe requires complex construction and is particularly expensive to manufacture. Furthermore, such a safety design fails to address the possibility of injury occurring before the injection is given.

Another known method of preventing needlestick injury is to replace the tubular sheath, which is supplied with the syringe and protecting the needle. In particular, it is now recommended practice to not attempt to replace the sheath after the syringe has been used, because of the difficulty of placing the end of the needle accurately within the sheath. It is thought that the act of trying to re-sheath the needle has in fact been the cause of a significant number of needlestick injuries, as such a method requires the use of two hands and the operator can be inaccurate. Furthermore, the sheath can easily be removed again, so reoccurring injury is possible.

Yet another known needlestick prevention device is an automatic needle sheath mounted on the syringe barrel, the sheath being able to slide out to cover the needle. Such construction generally includes a stationary sheath part and a movable sheath part spring-biased to an extended position in which it covers the needle. The movable sheath part retracts to expose the needle for use, and when the retracting pressure is released the spring moves it automatically into its extended position, where it is locked. The movable sheath part has a projection received in a track in the stationary part to determine its movement and to lock it. However, in one embodiment, the track is configured such that the movable sheath part can be unlocked by twisting it relative to the stationary part, and in another its movement is dictated by the track, so that the user has no choice about its subsequent use.

BRIEF SUMMARY OF THE INVENTION

The present invention provides various embodiments of a multi-component safety needle cover for use with injection devices, such as syringes, wherein the safety needle cover is configured to prevent needlestick injury by securely covering the needle prior to use and/or after use thereof. The safety needle cover is a relatively simple design comprising two cover members, an outer cover member and an inner cover member coupled to one another in a concentric manner. In particular, the outer cover member includes a cavity shaped and sized to receive a majority of the inner cover member within. The inner cover member also includes a cavity configured to enclose a needle extending from a delivery device to which the safety needle cover is directly coupled to.

In one embodiment, a safety needle cover consistent with the present disclosure comprises at least a first configuration, in which a user can manipulate the cover in such a manner so as to gain access to the needle (i.e., expose the needle) for administering a therapeutic agent. For example, each of the inner and outer cover members have an opening or port extending along a longitudinal length thereof, generally in alignment with a length of the needle when the cover is in the first configuration. The inner and outer cover members are rotatably coupled to one another so as to allow each cover member to rotate relative to one another while remaining coupled to one another. The inner cover member includes a first protrusion extending from an exterior surface on one side of the inner cover member and the outer cover member includes a corresponding aperture or recess configured to receive the protrusion therein. When in the first configuration, the first protrusion of the inner cover member is engaging and positioned within the aperture of the outer cover member, thereby preventing the inner and outer cover members from freely rotating relative to one another and further ensuring that the openings or ports of each of the inner and outer cover members are aligned with one another. The inner cover member further includes a hinge portion adjacent to a distal portion of the inner cover member, wherein the hinge couples the distal portion of the inner cover member to a proximal section of the inner cover member. Upon sufficient application of force to the safety needle cover, the hinge allows for the assembled inner and outer cover members to be displaced at the hinge and exposes the needle, which is able to pass through the openings or ports of the inner and outer cover members as the inner and outer cover members are displaced to the side.

Upon administering the therapeutic agent, a user need only bend the cover back into position over the needle. In the event that the delivery device is intended for single use only, a user can than then further manipulate the cover so as to permanently enclose the needle within the cover. Accordingly, the safety needle cover comprises a second configuration in which a user can manipulate the cover in such a manner so as to permanently enclose the needle and prevent subsequent access to the needle, thereby preventing the risk of re-use of the needle and inadvertent needle stick. The inner cover member further includes a second protrusion extending from an exterior surface of a side of the inner cover member generally opposite the first protrusion (i.e., approximately 180 degrees). It should be noted that the first protrusion is constructed in such a manner so as to sufficiently engage the aperture of the outer cover member to prevent free rotation of the inner and outer cover members relative to one another but has a relatively shallow profile which will allow the first protrusion to disengage from the aperture upon application of sufficient torque to the outer cover member. Accordingly, a user need only rotate the outer cover member approximately a half rotation, at which point, the second protrusion will engage and be received within the aperture. Unlike the first protrusion, however, the second protrusion may include a biasing member for applying a biasing force in an outward direction (i.e., away from the inner cover member and towards the outer cover member), thereby locking the second protrusion within the aperture and preventing disengagement. When the second protrusion is in engagement with the aperture, the opening or port of the outer cover member is no longer aligned with the corresponding opening or port of the inner cover member. Rather, the openings or ports of the inner and outer cover members are substantially opposing one another, which effectively creates a complete enclosure of the needle.

Although each of the inner cover member and outer cover member are separate from one another during actual formation (i.e., in their respective molds), the manufacturing method includes assembling the inner and outer cover members with one another during molding process via an in-mold assembly process. For example, the mold assembly may be arranged such that, as a result of in-mold alignment, during the ejection process, the outer cover member may be ejected in a direction towards the inner cover member, or vice versa, such that the two cover members engage one another and thereby form the assembly safety cover member, which provides for a lower cost of production and manufacture.

BRIEF DESCRIPTION OF THE DRAWINGS

FIG. 15B illustrates the corresponding stopping members formed on opposing ends of the hinge member configured to prevent over extension of the cover when transitioning from the closed position to the open position.

DETAILED DESCRIPTION OF THE INVENTION

By way of overview, the present invention provides a multi-component safety needle cover for use with injection devices, such as syringes, wherein the safety needle cover is configured to prevent needlestick injury by permanently covering the needle after use thereof.

Figure 1:
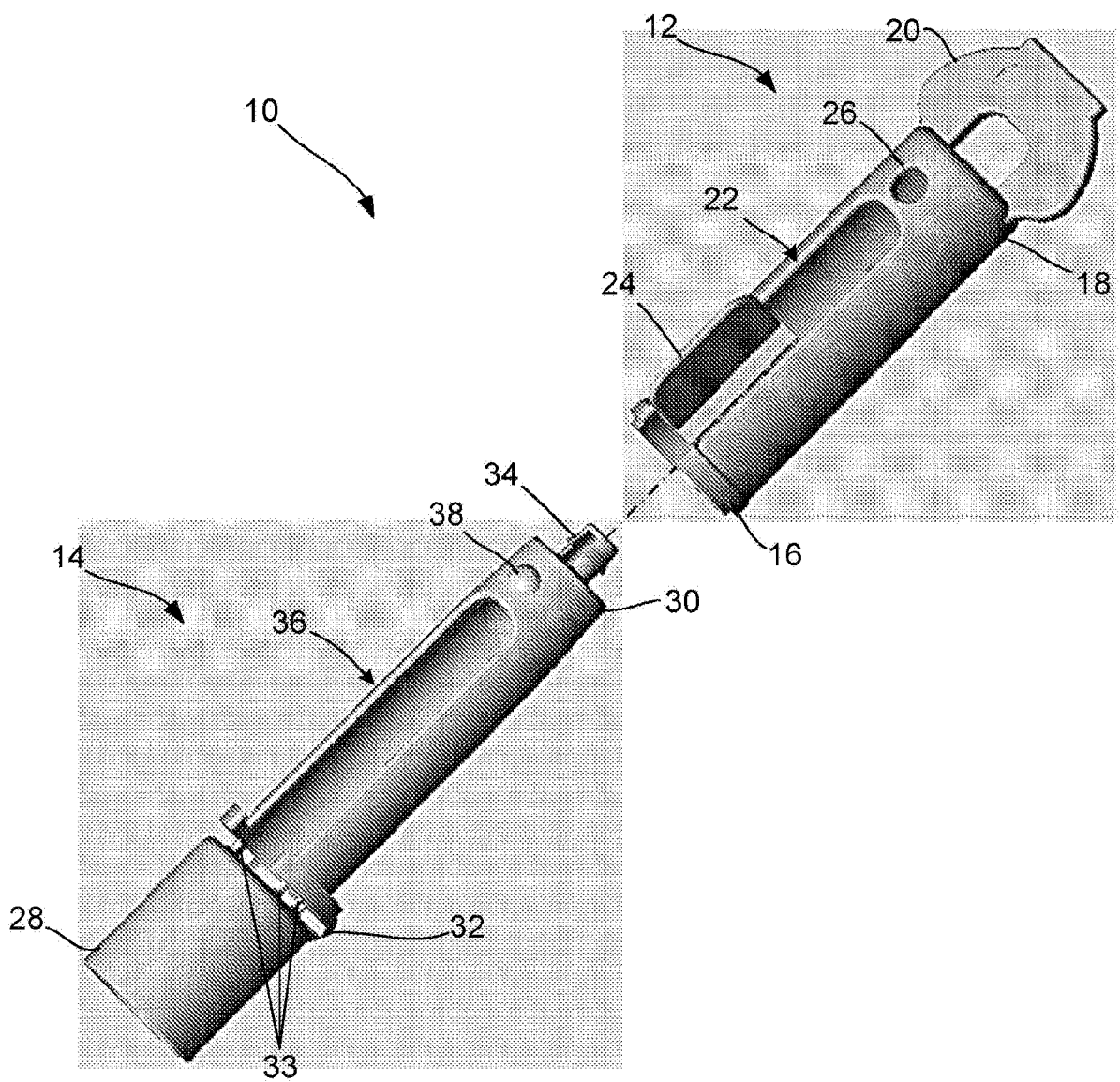
FIG. 1 is a front perspective exploded view of one embodiment of a safety needle cover consistent with the present disclosure illustrating inner and outer cover members separated from one another.
Figure 2:
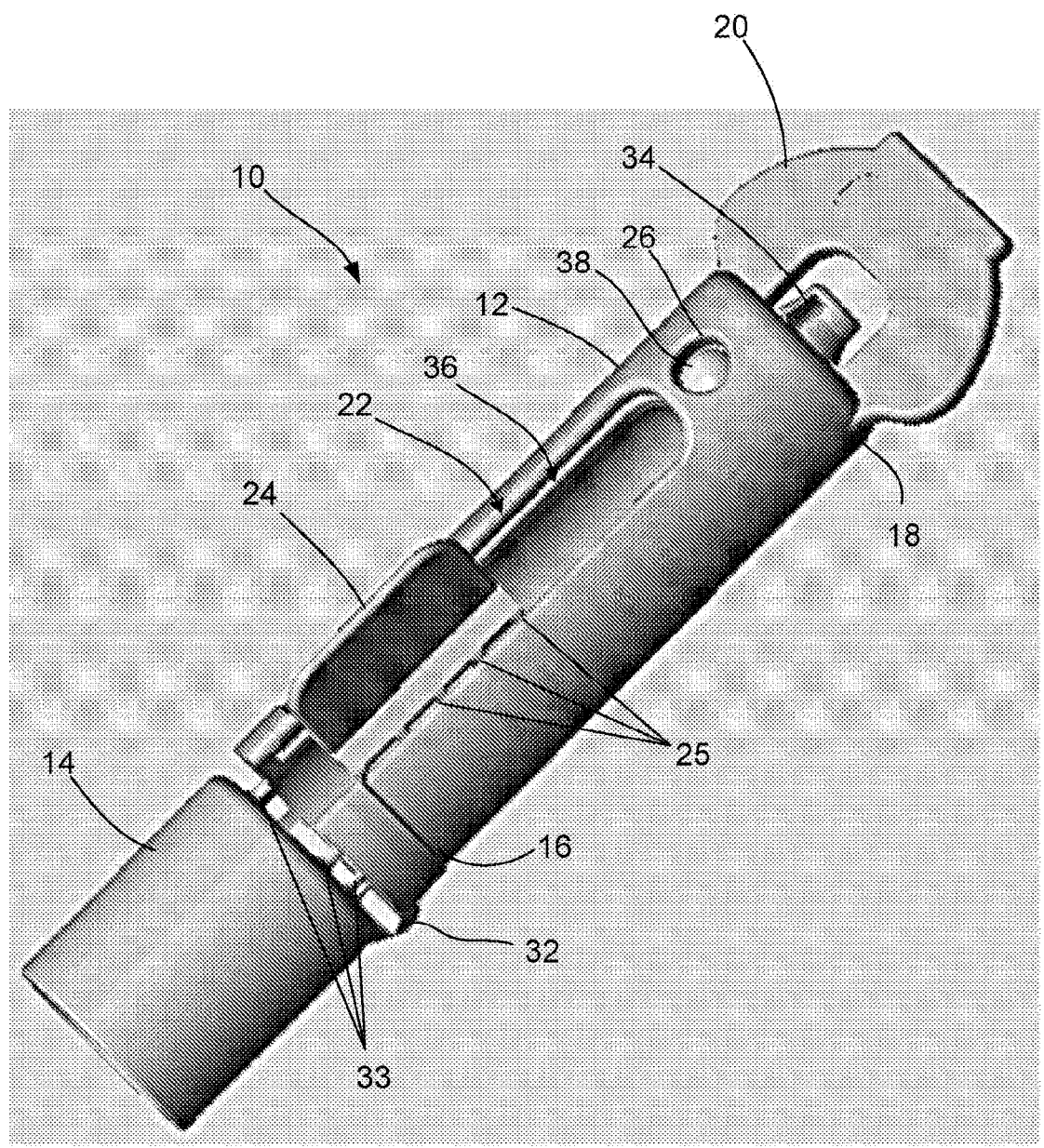
FIG. 2 is a front perspective view of the safety needle cover of FIG. 1 illustrating the inner and outer cover members assembled with one another.
Figure 3:
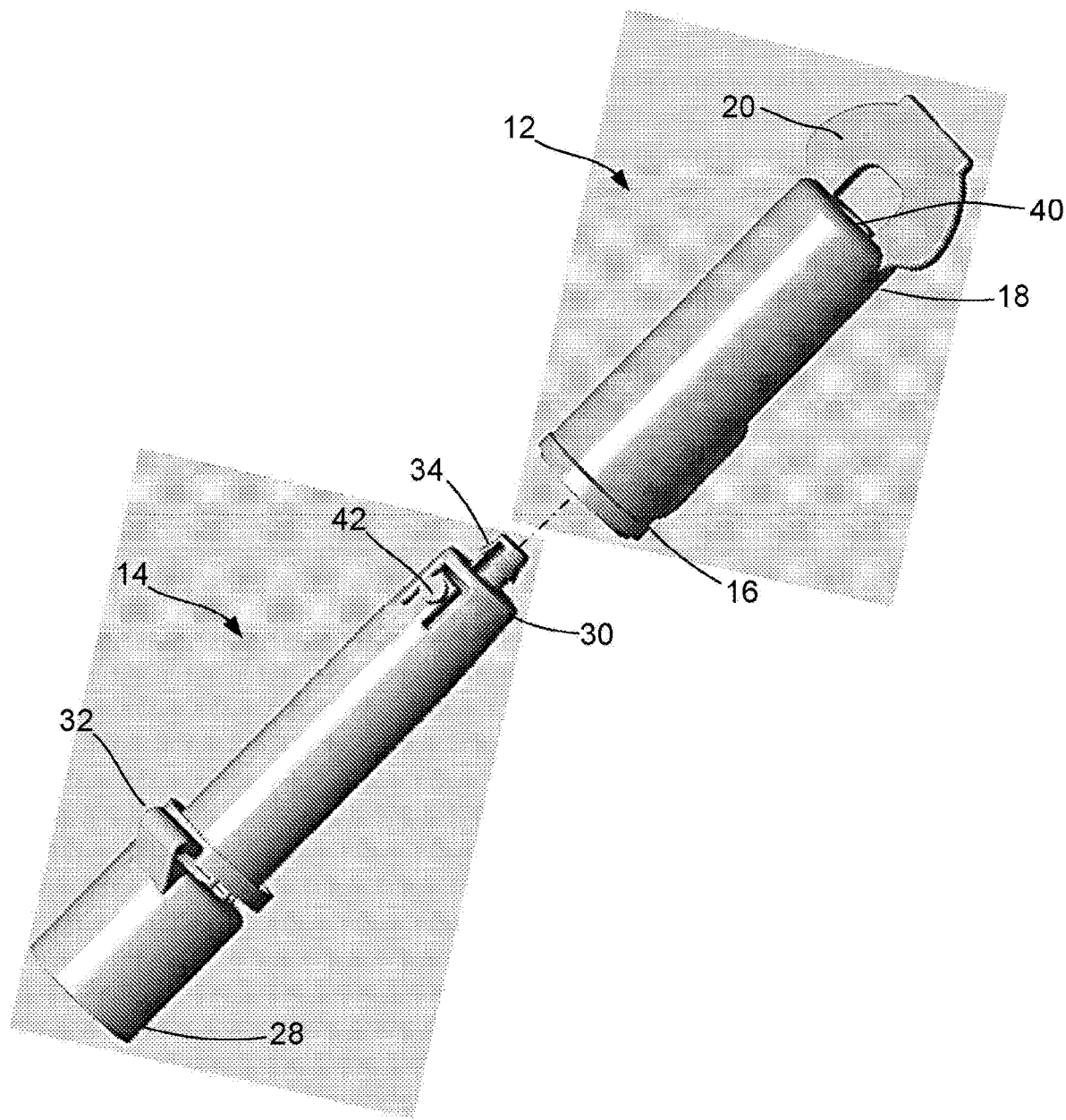
FIG. 3 is a rear perspective exploded view of the safety needle cover of FIG.
Figure 4:
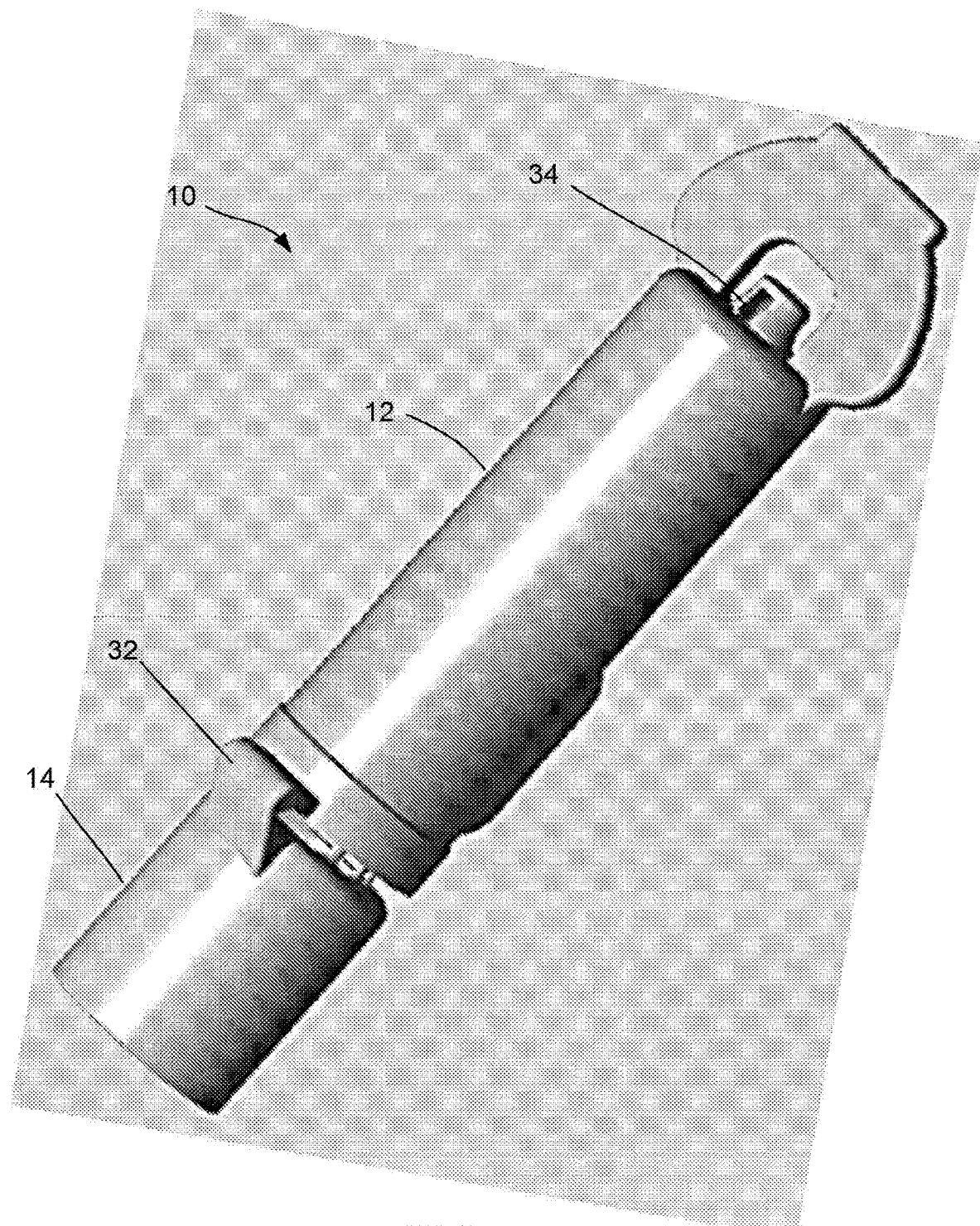
FIG. 4 is a rear perspective view of the safety needle cover of FIG. 3 illustrating the inner and outer cover members assembled with one another.
Figure 5:
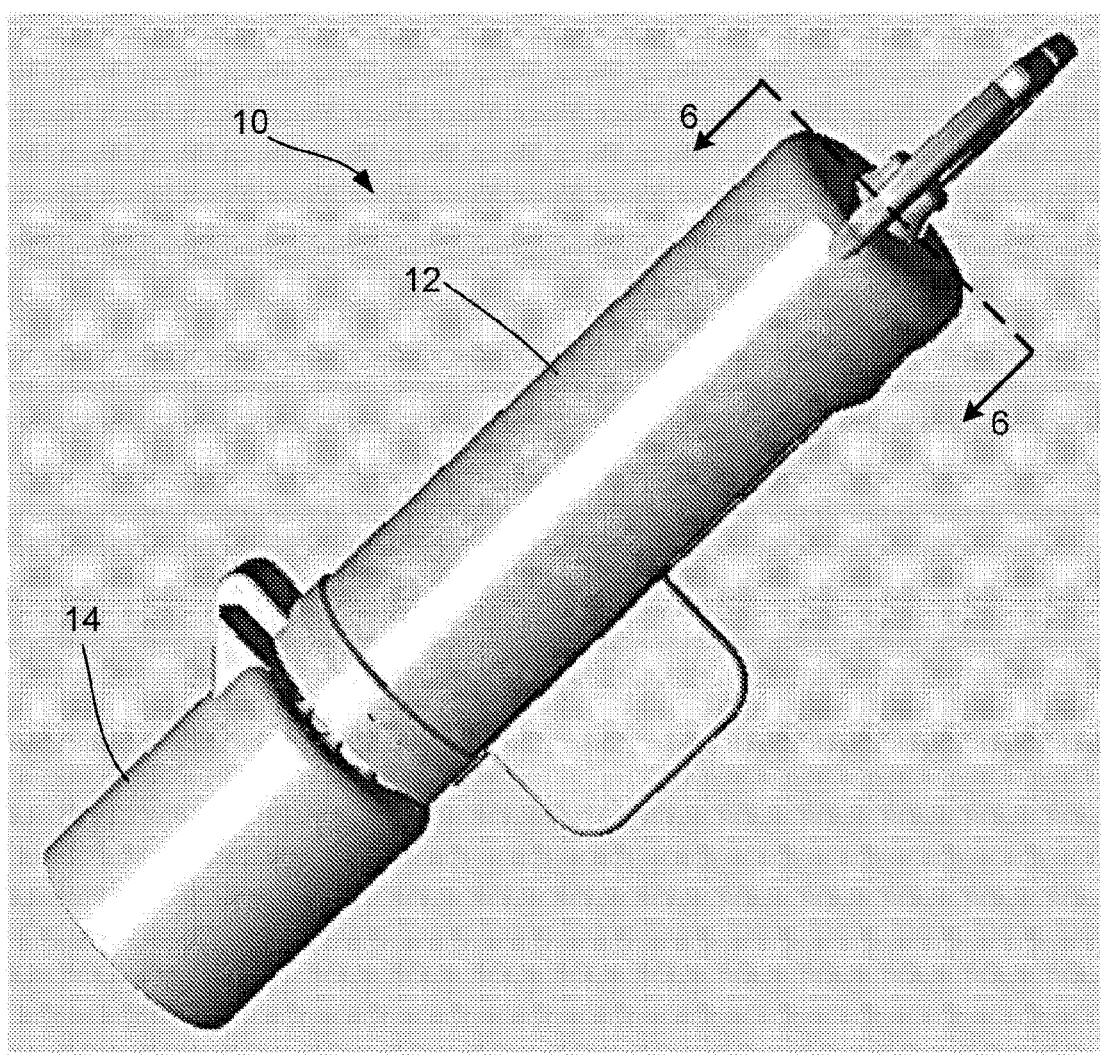
FIG. 5 is another perspective view of the safety needle cover of FIG. 1.
Figure 6:
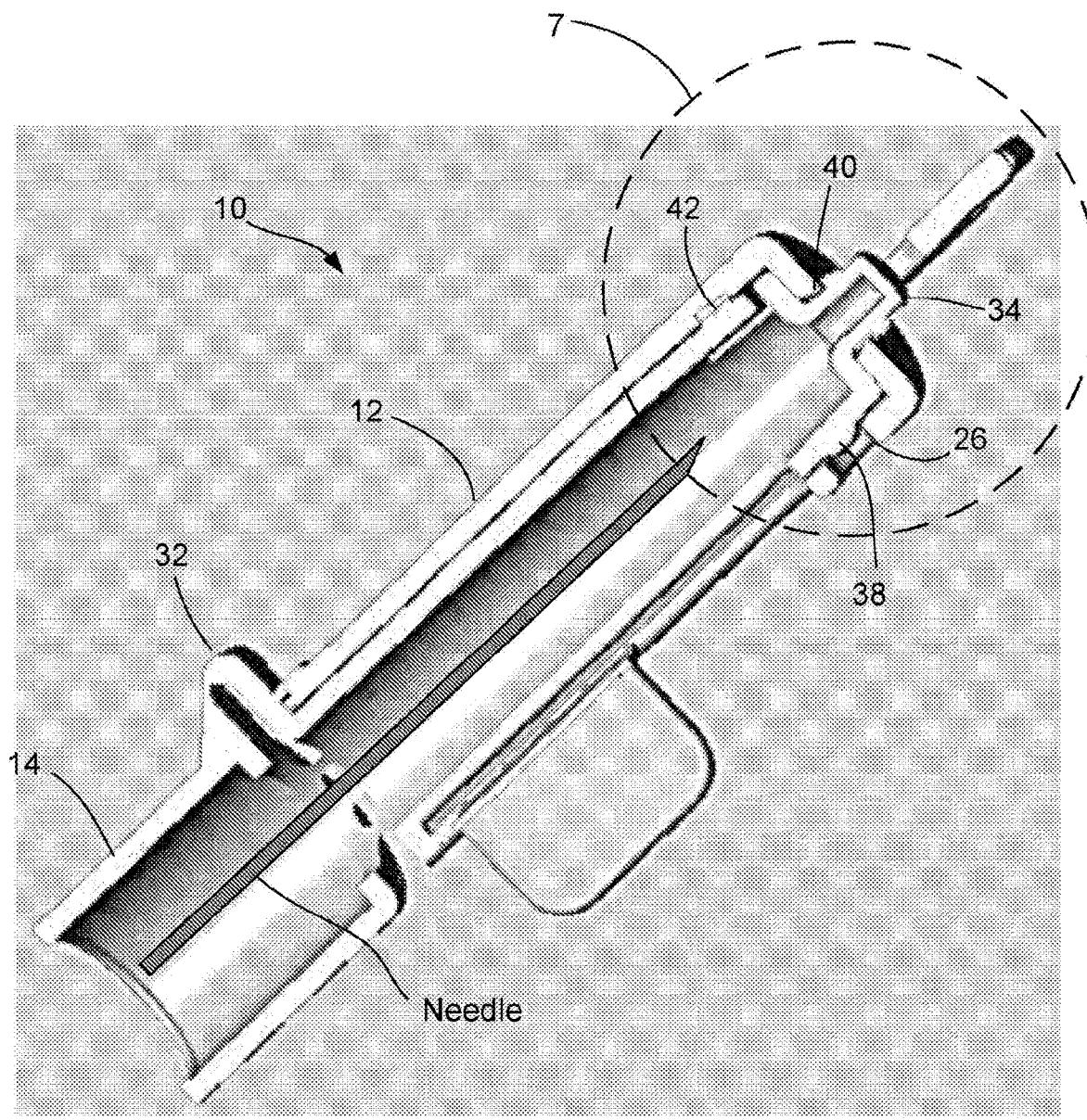
FIG. 6 is a perspective view, partly in section, of the safety needle cover taken along lines A-A in FIG. 5.
Figure 7:
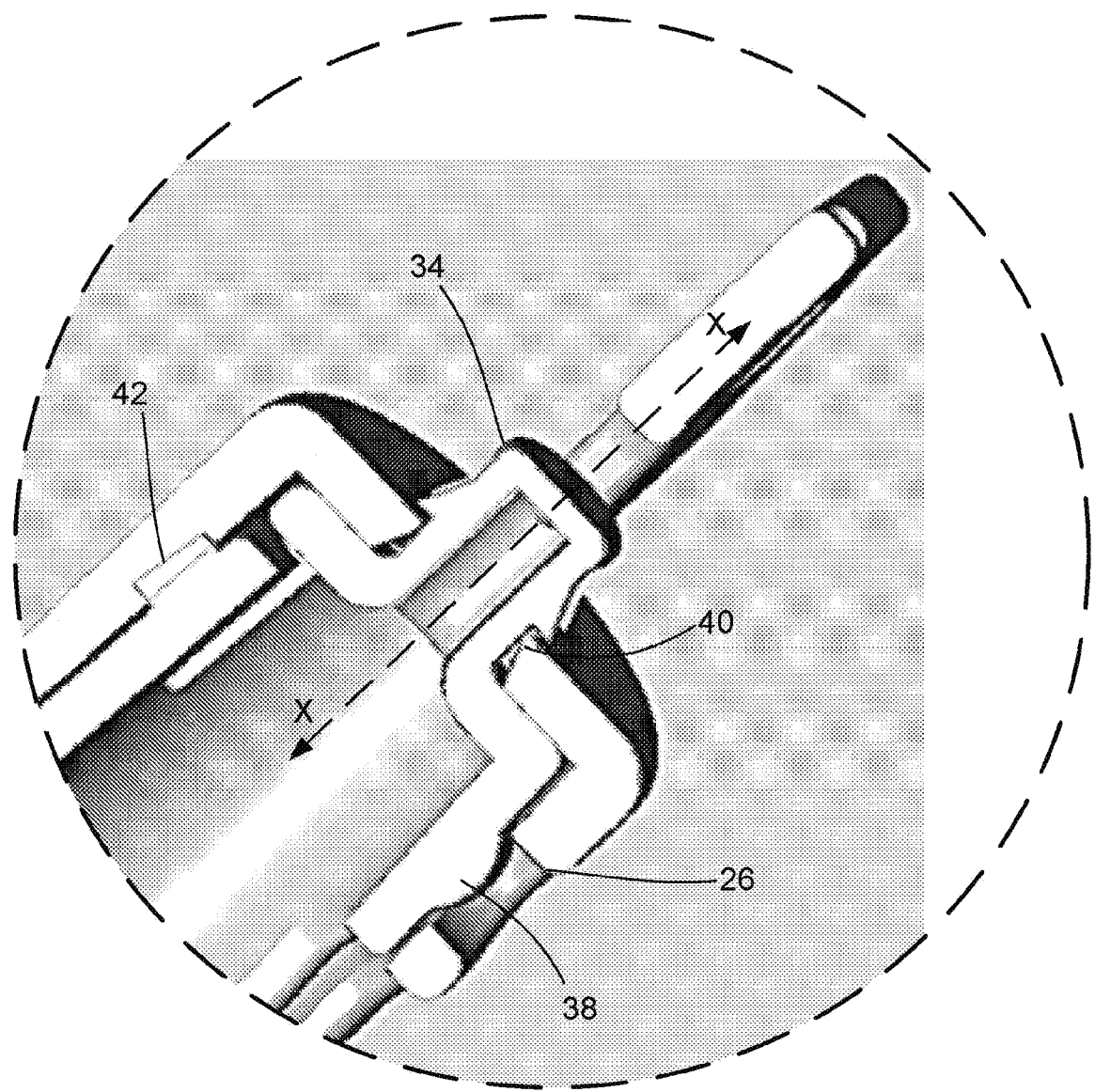
FIG. 7 is an enlarged perspective view, partly in section, illustrating the distal ends of the assembled inner and outer cover members.
Figure 8:
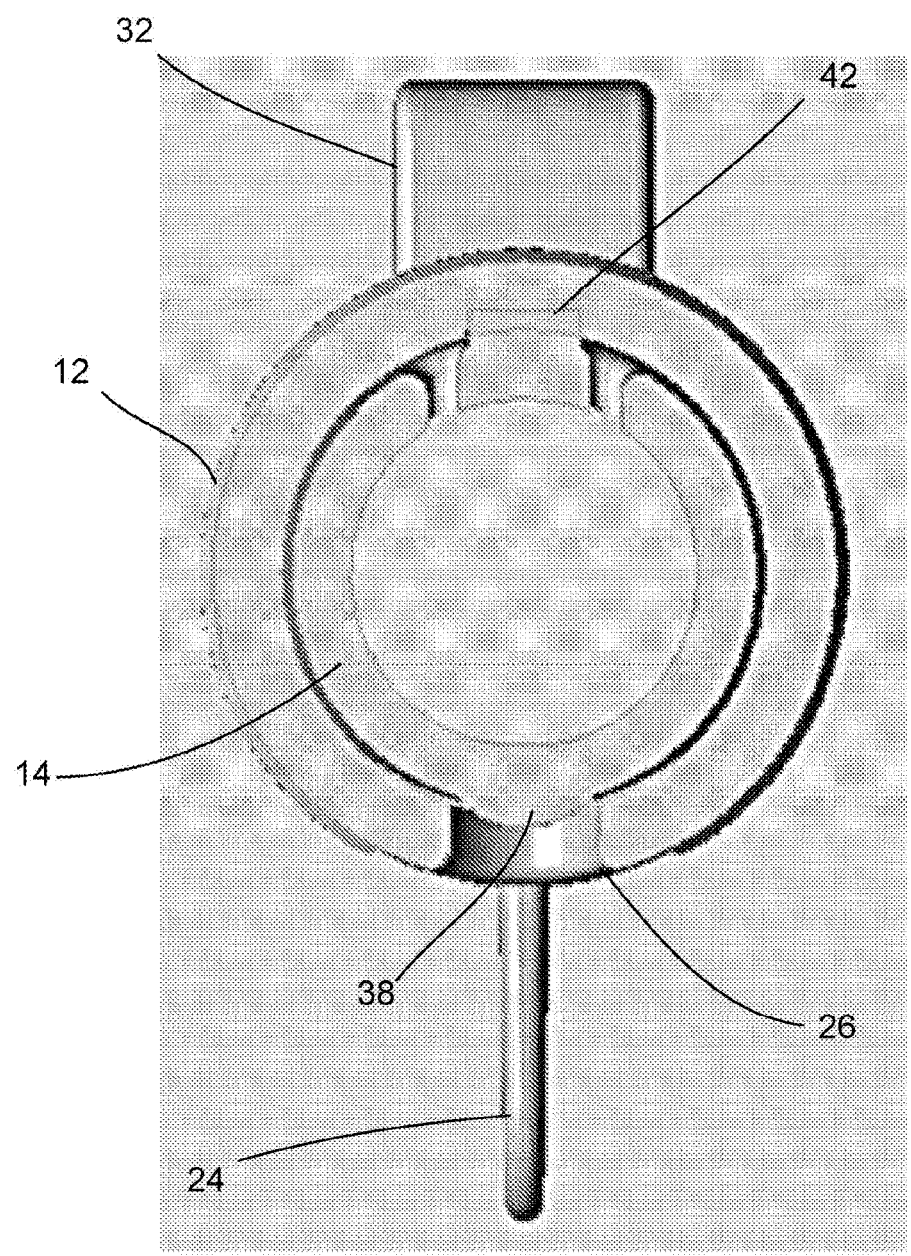
FIG. 8 is a sectional view of the safety needle cover illustrating the engagement of the first protrusion of the inner cover member with the aperture of the outer cover member.

FIG. 1 is a perspective exploded view one embodiment of a safety needle cover 10 consistent with the present disclosure. The safety needle cover 10 is a relatively simple design comprising two cover members, an outer cover member 12 and an inner cover member 14 coupled to one another in a concentric manner (as shown in FIGS. 6 and 8). In particular, the outer cover member 12 includes a cavity shaped and sized to receive a majority of the inner cover member 14 within. The inner cover member also includes a cavity configured to enclose a needle extending from a delivery device to which the safety needle cover is directly coupled to. FIG. 2 is a perspective view of the safety needle cover 10 illustrating the outer and inner cover members 12, 14 assembled with one another. FIG. 3 is another perspective exploded view of the safety needle cover 10 showing a rear side of the cover 10 and FIG. 4 illustrates the outer and inner cover members 12, 14 coupled to one another. FIG. 5 is another perspective view of the safety needle cover 10. FIG. 6 is a perspective view, partly in section, of the safety needle cover 10 taken along lines A-A in FIG. 5. FIG. 7 is an enlarged perspective view, partly in section, illustrating the distal ends of the assembled inner and outer cover members. FIG. 8 is a front sectional view of the safety needle cover illustrating the engagement of the first protrusion of the inner cover member with the aperture of the outer cover member.

Figure 9B:
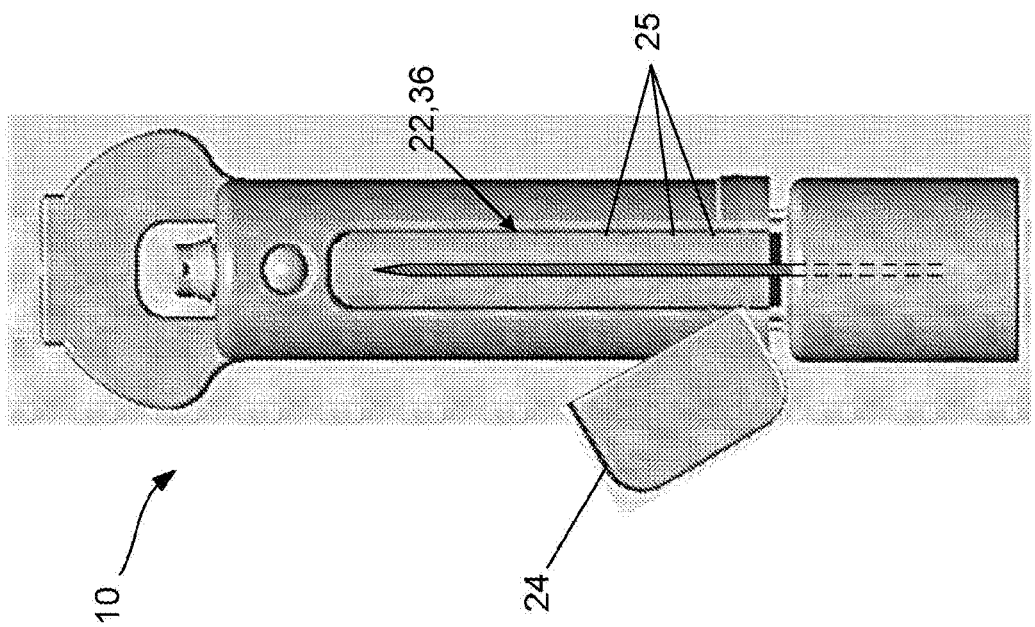
FIGS. 9A, 9B, 9C, and 9D illustrate transitioning from the first configuration, in which the safety needle cover allows for use of the delivery device (i.e., administration of a therapeutic agent via needle injection), to the second configuration, in which the cover is permanently locked and the needle is enclosed within.
Figure 9A:
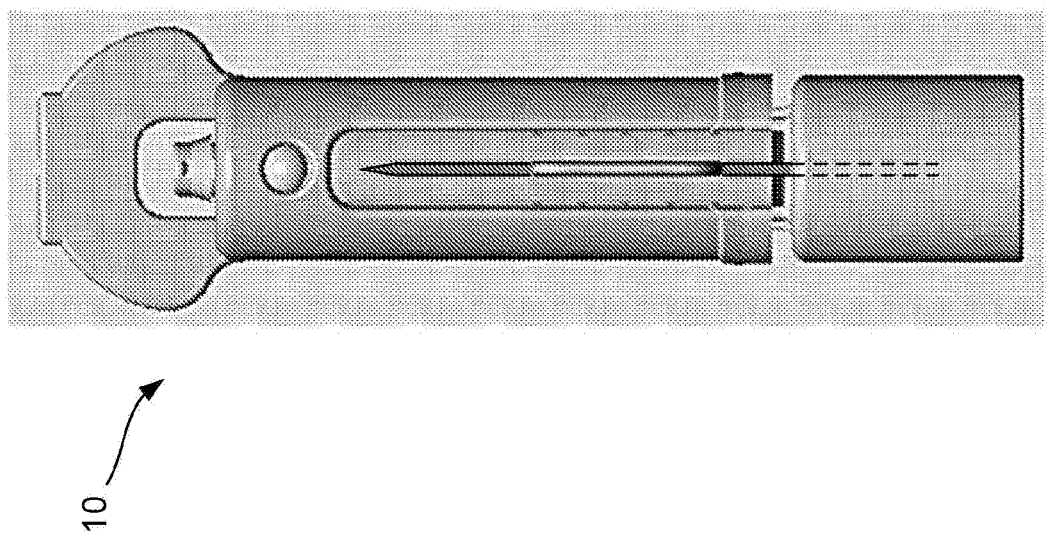
Figure 9D:
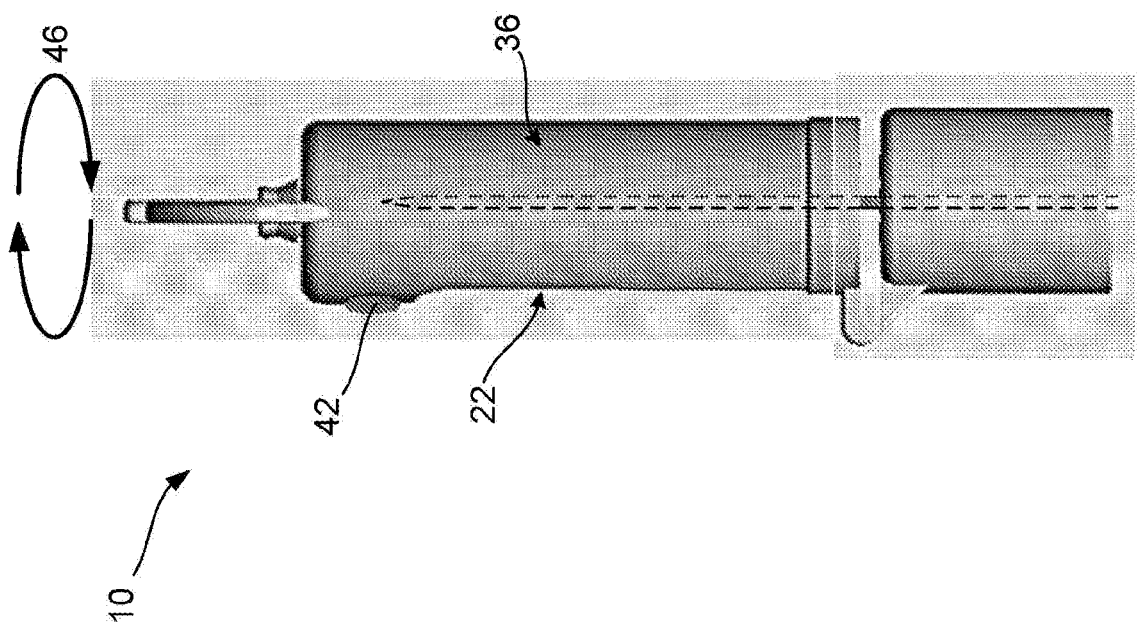
Figure 9C:
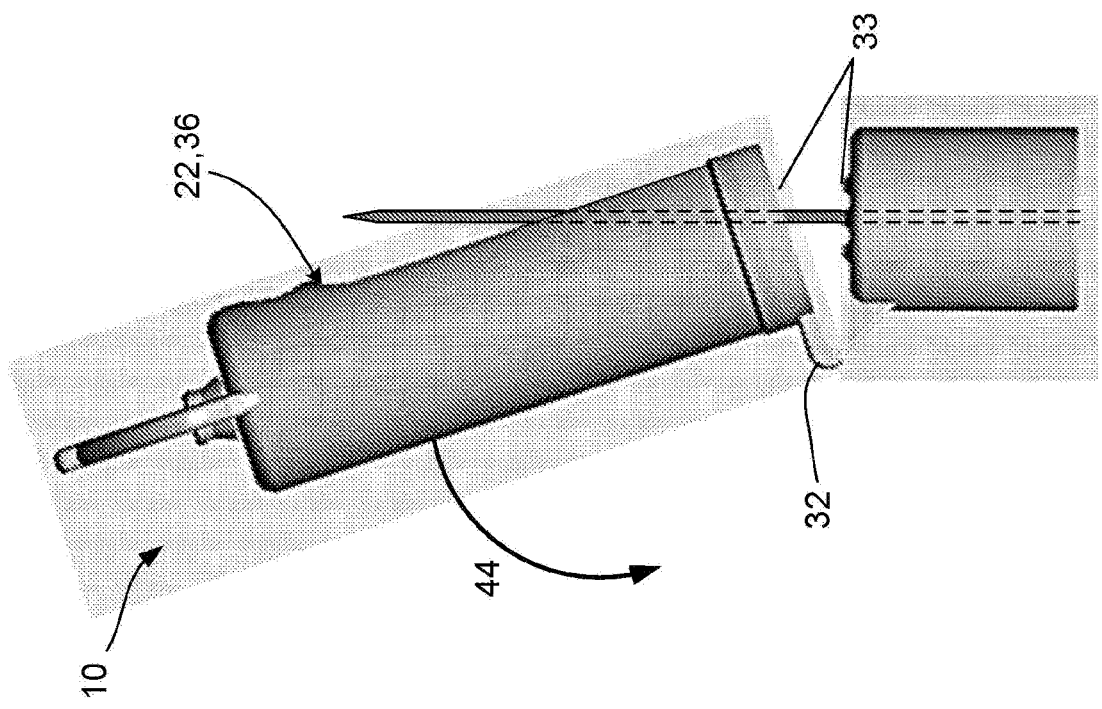

As shown, the outer cover member 12 generally includes proximal end 16, a distal end 18, which includes a handle or grip 20 allowing for rotation of the outer cover member 12 relative to the inner cover member 14 when a user wishes to transition the cover 10 from a first configuration, in which the needle of the delivery device may be accessed, to second configuration, which essentially locks the outer and inner cover members 12, 14 to one another, as will be described in greater detail herein. The outer cover member 12 further includes an opening or port 22 extending along a length thereof. The opening or port 22 is configured to allow a needle to pass therethrough when the cover 10 bends along a hinge, as will be described herein. For example, as shown, the opening 22 extends a length from the proximal end 16 towards the distal end 18 that generally corresponds to a length of the needle extending within the cover members. The outer cover member 12 further includes a breakaway tab member 24 positioned within the opening 22 of the outer cover member 12. The breakaway tab member 24 has perforations, scores, or other cut-outs along the sides 25 where the tab member 24 is coupled to the opening 22. Accordingly, the tab member 24 serves at least two purposes: 1) it is a safety feature in that the tab member 24 is a breakaway tab (able to be torn free from the opening 22), which indicates whether the cover 10 has been used or not and thus whether the needle is safe for use; and 2) it prevents the opening 22 from collapsing during manufacture (i.e., the tab 24 helps keep index of the outer cover member 12 and the opening 22 during the molding process). The outer cover member 12 further includes at least a first aperture 26 configured to receive corresponding first and second protrusions formed the inner cover member 14, as will be discussed herein. The inner cover member 14 includes a proximal portion 28 and a distal portion 30, which are generally separated by a hinge member 32. The hinge member 32 is a living hinge, thereby allowing for repeated movement between a closed configuration (as shown when the outer and inner cover members 12, 14 are closed over the needle) and an open configuration (as shown in FIG. 9C when the outer cover member 12 and a portion of the inner cover member 14 (e.g., distal portion 30) are bent out of plane with the needle to allow for needle use). In some embodiments, the hinge member 32 may be molded in such a manner so that the default shape is in the closed configuration such that the hinge member 32 has shape memory to cause the outer cover member 12 and portion of the inner cover member 14 to return to the default shape so as to cause the needle to be covered. In some embodiments, the hinge member 32 may include a shape memory material. It should be noted that the proximal and distal portions 28, 30 of the inner cover member 14 are further coupled to one another in a breakaway fashion. In particular, the connection 33 between the proximal and distal portions 28, 30 includes perforations, scores, or other cut-outs, thereby allowing for the distal portion 30 of the inner cover member 14 to break away from the proximal portion 28 when a user moves the cover from the closed position to the open position. The connection 33 serves at least two purposes: 1) it is a safety feature in that the perforated or scored connection 33 serves as a breakaway connection, which indicates whether the cover 10 has been used or not and thus whether the needle is safe for use; and 2) it prevents the proximal portion 28 and distal portion 30 from collapsing during manufacture (i.e., the connection 33 helps keep index of the inner cover member 14 throughout its length during the molding process).

The inner cover member 14 further includes a pin 34 extending from the distal portion 30, wherein the pin 34 is configured to be received and retained within a corresponding bore 40 in the distal end 18 of the outer cover member 12 and further allow the inner and outer cover members to be rotatably coupled to one another about a longitudinal axis of the pin 34. The inner cover member 14 further includes an opening or port 36 extending along a length thereof. The opening 36 is similarly configured as the opening 22 of the outer cover member 12. For example, as shown, the opening 36 extends a length from the proximal end 28 towards the distal end 30 that generally corresponds to a length of the needle extending within the cover members and further resembles the opening 22 of the outer cover member 12. Accordingly, when the openings 22, 36 of the outer and inner cover members 12, 14 are aligned with one another, the openings 22, 36 are configured to allow a needle to pass therethrough when the cover 10 bends along the hinge 32. The inner cover member 14 further includes a first protrusion 38 and a second protrusion 42, each extending from an exterior surface on opposing sides of the inner cover member 14. The first and second protrusions 38, 42 allow for the cover 10 to be placed in two different configurations, as described below and illustrated in FIGS. 9A-9D.

FIGS. 9A, 9B, 9C, and 9D illustrate transitioning from the first configuration to the second configuration. The safety needle cover comprises at least a first configuration shown in FIGS. 9A, 9B, and 9C, in which a user can manipulate the cover in such a manner so as to gain access to the needle (i.e., expose the needle) for administering a therapeutic agent. For example, as previously described, the outer cover member 12 and the inner cover member 14 each have an opening 22, 36, respectively, extending along a longitudinal length thereof, generally in alignment with a length of the needle when the cover is in the first configuration. The inner and outer cover members are rotatably coupled to one another (via engagement between pin 34 of the inner cover member 14 and the bore 40 of the outer cover member 12) so as to allow each cover member to rotate relative to one another while remaining coupled to one another. The inner cover member 14 includes a first protrusion 38 extending from an exterior surface on one side of the inner cover member 14 and the outer cover member 12 includes a corresponding aperture or recess 26 configured to receive the first protrusion 38 therein. When in the first configuration, the first protrusion 38 of the inner cover member 14 is engaging and positioned within the aperture 26 of the outer cover member 12, thereby preventing the inner and outer cover members from freely rotating relative to one another and further ensuring that the openings of each of the inner and outer cover members are aligned with one another. The inner cover member 14 further includes a hinge member 32 coupling the proximal and distal portions 28, 30 of the inner cover member 14 to one another. When a user is ready to expose the needle so as to administer a therapeutic agent via injection, the user need only remove the breakaway tab 24 (shown in FIG. 9B) and apply sufficient application of force to the safety needle cover, specifically at the distal portion 30, at which point the perforated connection 33 will break away and the assembled inner and outer cover members will to bend relative to the proximal portion 28 of the inner cover member at the hinge 32, as shown in FIG. 9C. As the assembly inner and outer cover members bend, as indicated by arrow 44, the needle is exposed and able to pass through the aligned openings of the inner and outer cover members as the inner and outer cover members are displaced to the side.

Upon administering the therapeutic agent, a user need only bend the assembled inner and outer cover members to a closed position over the needle. In the event that the delivery device is intended for single use only, a user can than then further manipulate the cover so as to permanently enclose the needle within to prevent subsequent access to the needle, thereby preventing the risk of re-use of the needle and inadvertent needlestick. For example, as shown in FIG. 9D, the safety needle cover 10 comprises a second configuration in which a user can manipulate the cover in such a manner so as to permanently enclose the needle by simply twisting the inner and outer cover members relative to one another until the second protrusion 42 of the inner cover member 14 engages the aperture 26 of the outer cover member 12. The second protrusion 42 extends from an exterior surface of a side of the inner cover member 14 that is generally opposite the first protrusion 38 (i.e., approximately 180 degrees). Accordingly, a user need only twist the outer cover member 12 half of a full rotation (i.e., 180 degrees) about the longitudinal axis X, as indicated by arrow 46, to set the second protrusion 42 of the inner cover member 14 within the aperture 26 of the outer cover member.

It should be noted that the first protrusion 38 is constructed in such a manner so as to sufficiently engage the aperture of the outer cover member to prevent free rotation of the inner and outer cover members relative to one another but has a relatively shallow profile which will allow the first protrusion 38 to disengage from the aperture 26 of the outer cover member 12 upon application of sufficient torque to the outer cover member 12. Accordingly, a user need only rotate the outer cover member 12 approximately a half rotation, at which point, the second protrusion 42 will engage and be received within the aperture. Unlike the first protrusion 38, however, the second protrusion 42 may include a biasing member for applying a biasing force in an outward direction (i.e., away from the inner cover member 14 and towards the outer cover member 12), thereby locking the second protrusion 42 within the aperture 26 and preventing disengagement even when a user attempts to twist the outer cover member 12. When the second protrusion 42 is in engagement with the aperture 26, the opening 22 of the outer cover member 12 is no longer aligned with the corresponding opening 36 of the inner cover member 14.

Rather, the openings 22, 36 are substantially opposing one another on opposing sides of the cover, thereby effectively creating a complete enclosure of the needle within the inner and outer cover members.

Figure 10:
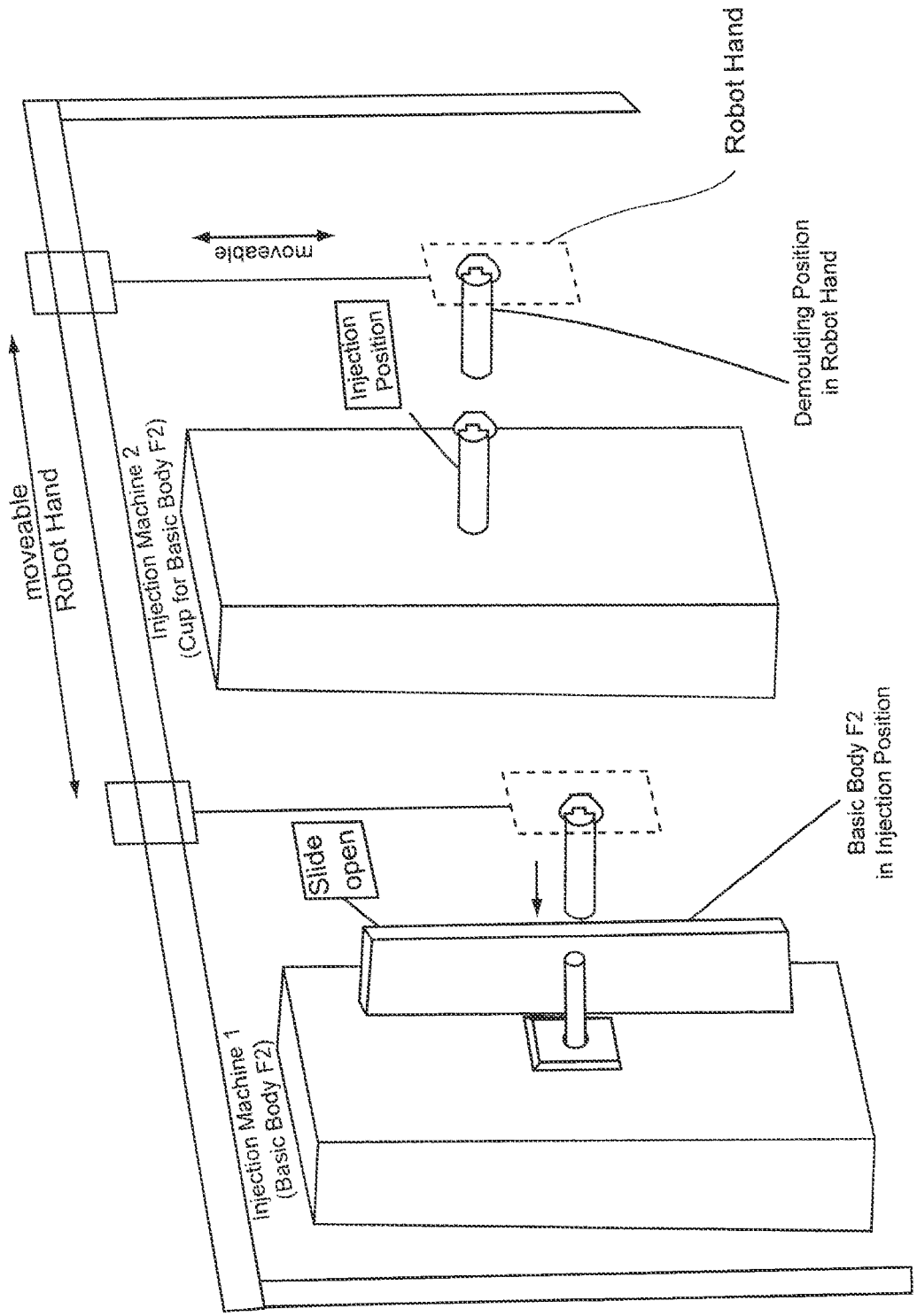
FIG. 10 is a schematic illustrating one embodiment of an in-mold manufacturing and assembly of the inner and outer cover members with one another.

FIG. 10 is a schematic illustrating one embodiment of an in-mold manufacturing and assembly of the inner and outer cover members with one another. As illustrated in FIG. 10, although each of the inner cover member and outer cover member are separate from one another during actual formation (i.e., in their respective molds), the manufacturing method includes assembling the inner and outer cover members with one another during molding process via an in-mold assembly process. For example, the mold assembly may be arranged such that, as a result of in-mold alignment, during the ejection process, the outer cover member may be ejected in a direction towards the inner cover member, or vice versa, such that the two cover members engage one another and thereby form the assembly safety cover member, which provides for a lower cost of production and manufacture.

Another embodiment of a safety needle cover 100 consistent with the present disclosure is illustrated in FIGS. 11-21. The safety needle cover 100 may include similar features and components or parts of the safety needle cover 10 of FIGS. 1-10 previously described herein. Accordingly, like parts may have similar reference numerals.

Figure 11:
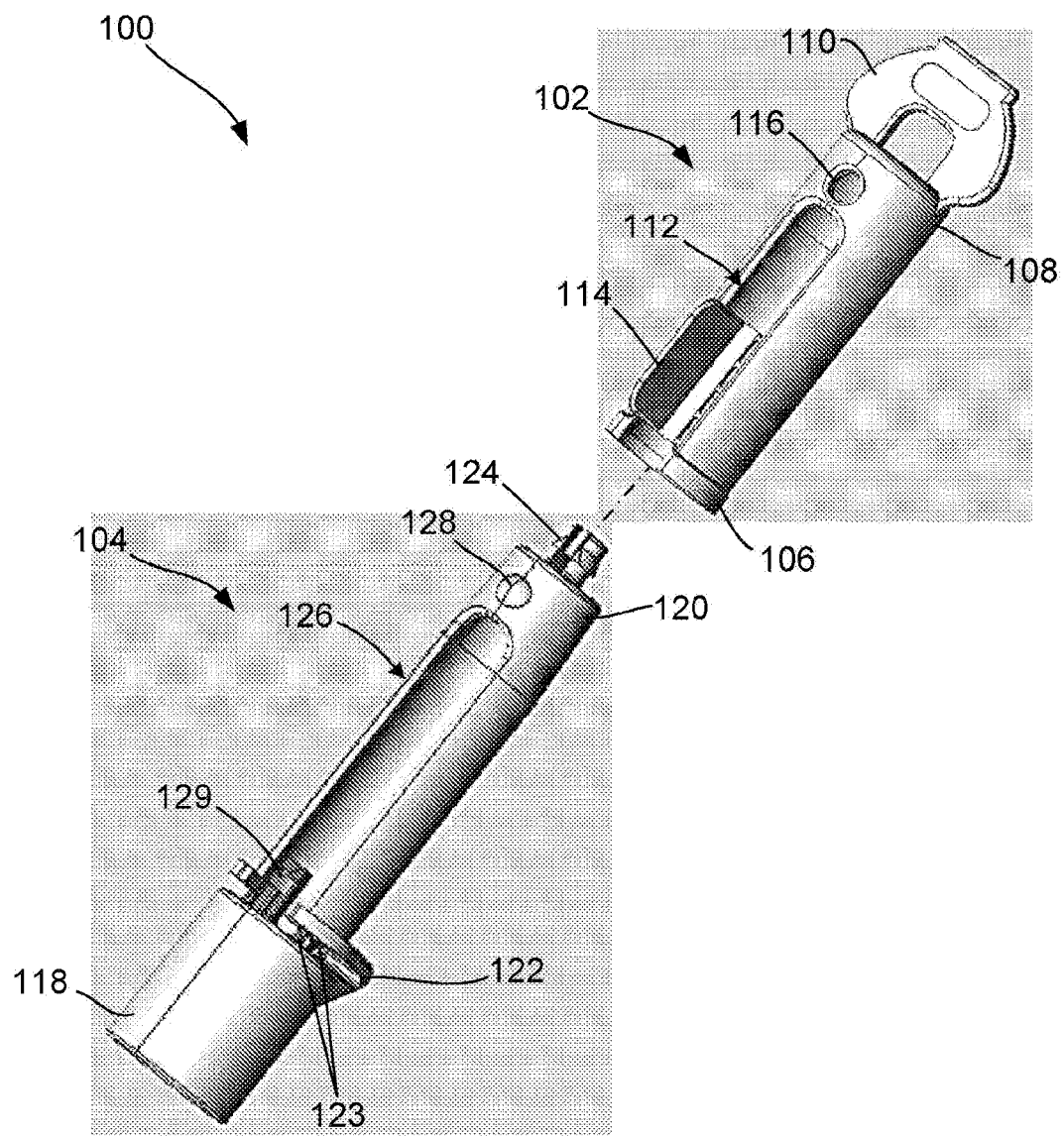
FIG. 11 is a front perspective exploded view of another embodiment of a safety needle cover consistent with the present disclosure illustrating inner and outer cover members separated from one another.

FIG. 11 is a front perspective exploded view of the safety needle cover 100 consistent with the present disclosure. The safety needle cover 100 is a relatively simple design comprising two cover members, an outer cover member 102 and an inner cover member 104 coupled to one another in a concentric manner. In particular, the outer cover member 102 includes a cavity shaped and sized to receive a majority of the inner cover member 104 within. The inner cover member 104 also includes a cavity configured to enclose a needle extending from a delivery device to which the safety needle cover is directly coupled to.

Figure 12:
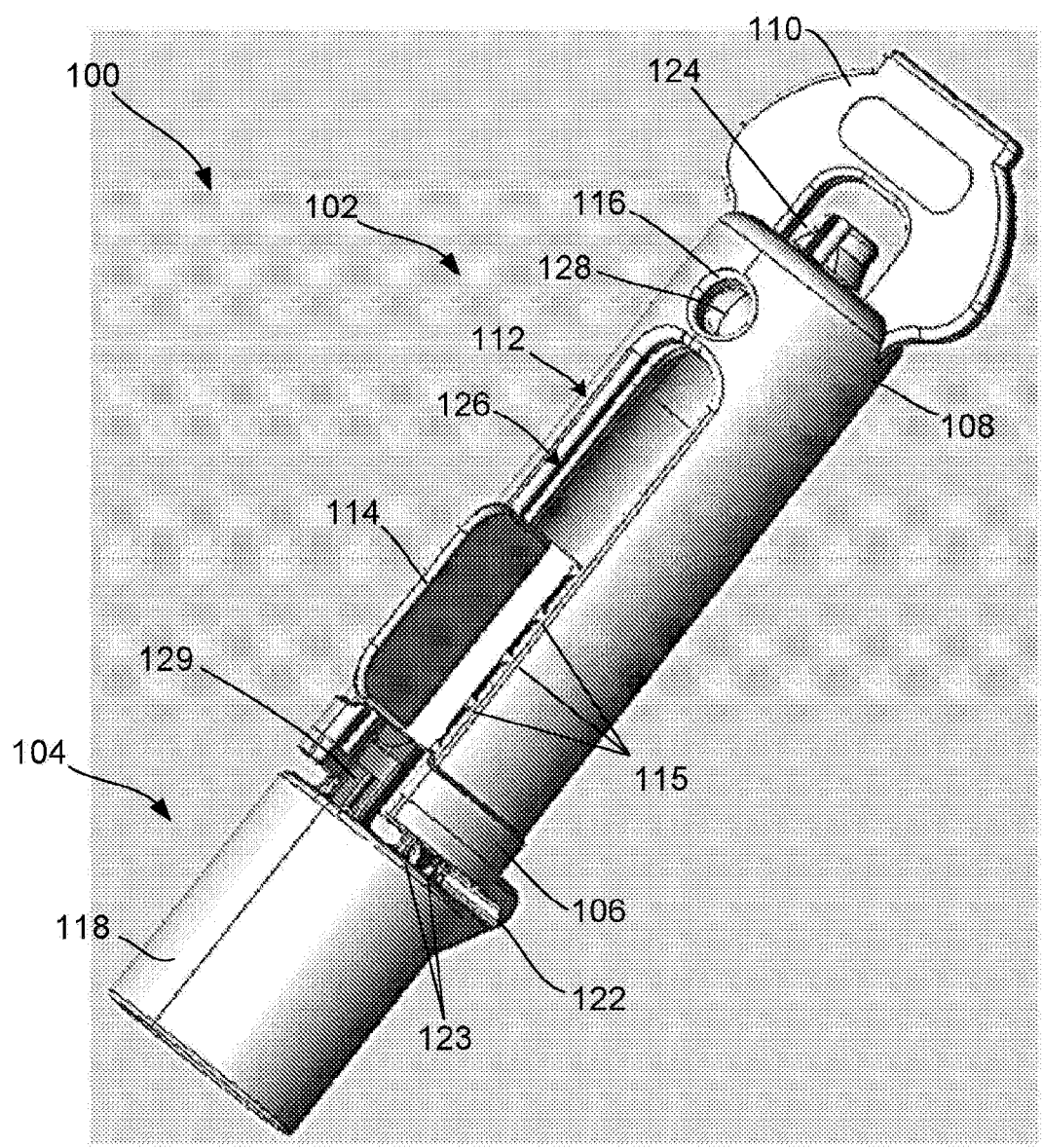
FIG. 12 is a front perspective view of the safety needle cover of FIG. 11 illustrating the inner and outer cover members assembled with one another.
Figure 13:
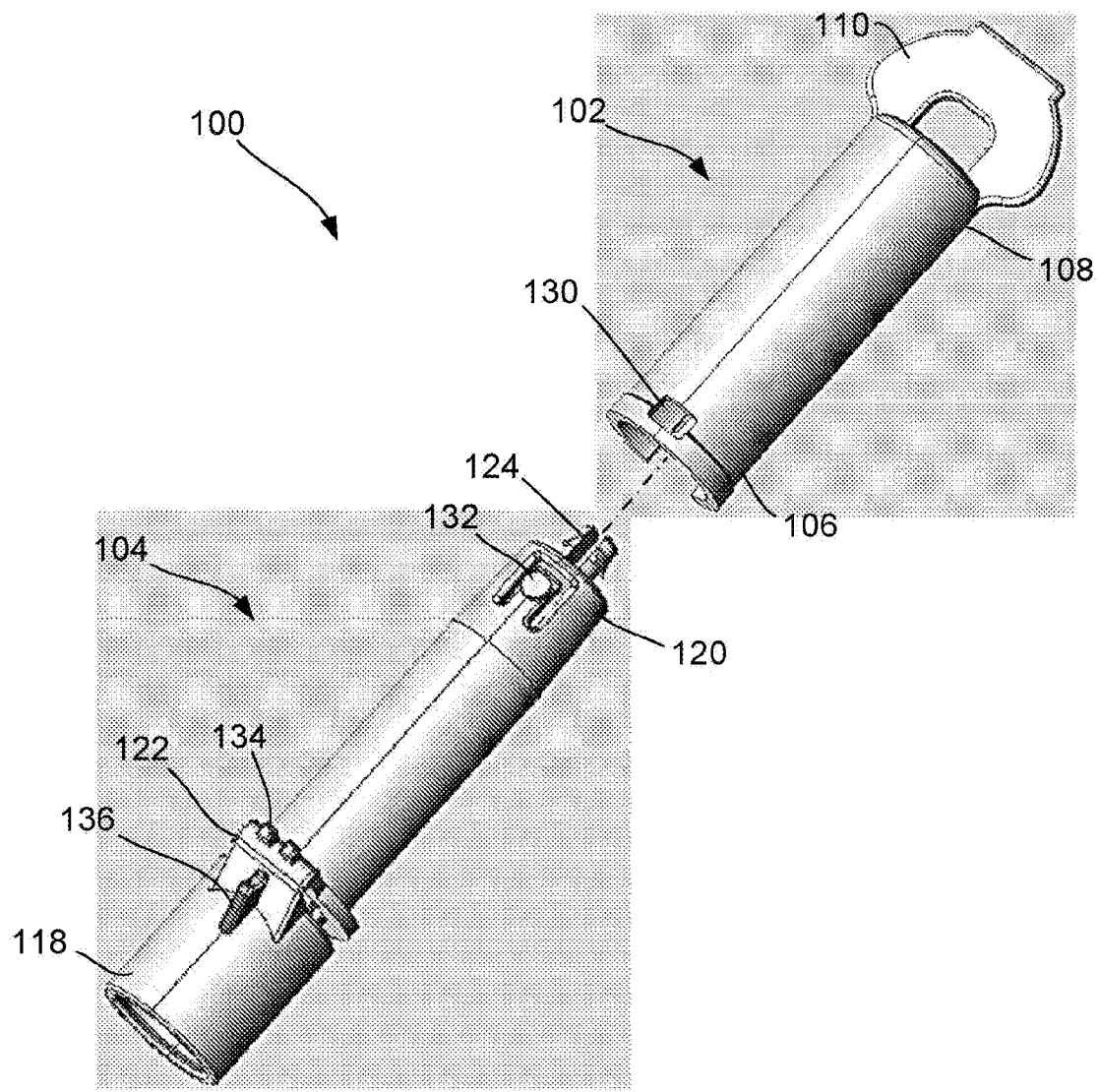
FIG. 13 is a rear perspective exploded view of the safety needle cover of FIG. 11.
Figure 14:
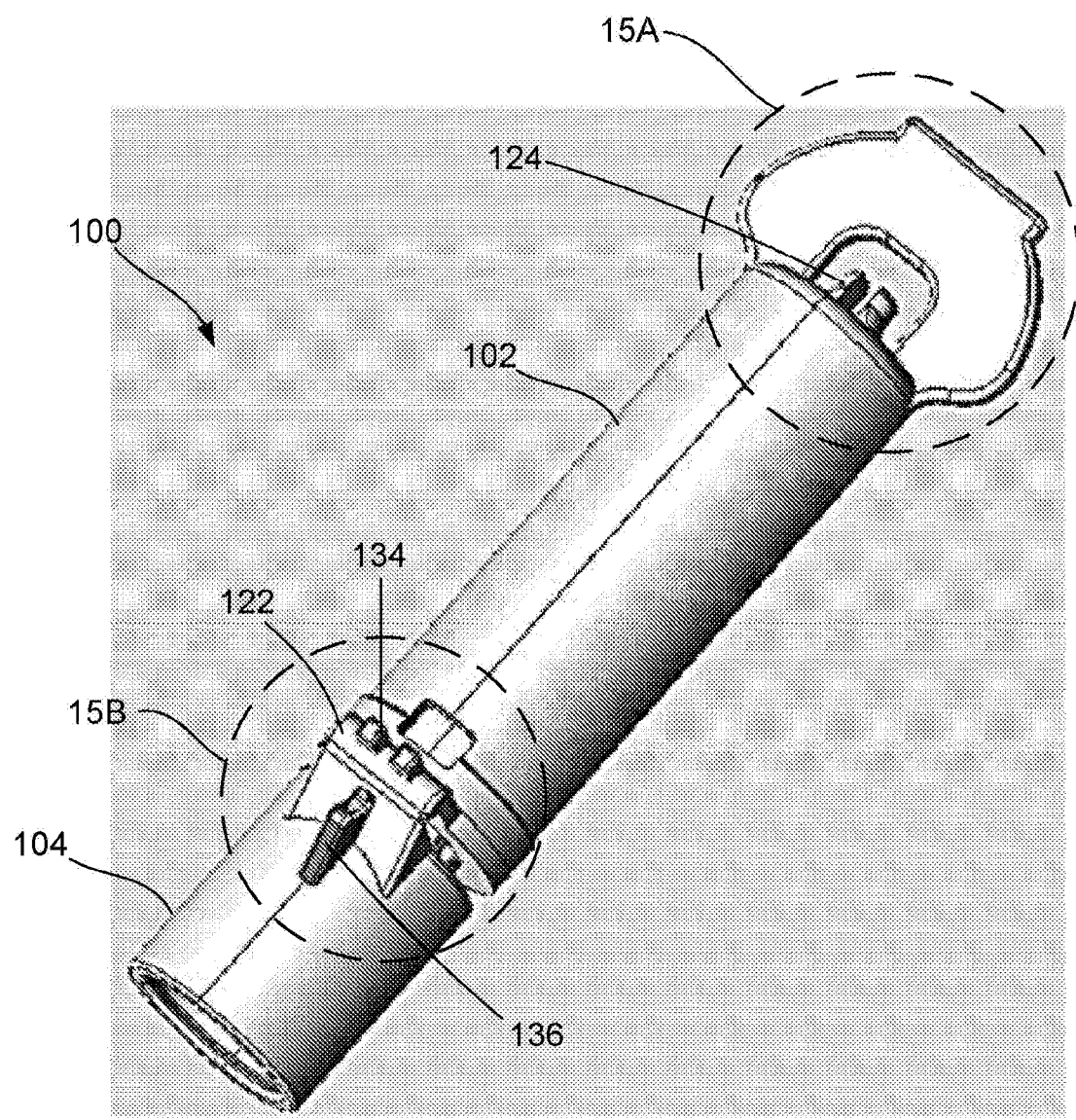
FIG. 14 is a rear perspective view of the safety needle cover of FIG. 13 illustrating the inner and outer cover members assembled with one another.

FIG. 12 is a front perspective view of the safety needle cover 100 illustrating the inner and outer cover members assembled with one another. FIG. 13 is a rear perspective exploded view of the safety needle cover 100 and FIG. 14 is a rear perspective view of the safety needle cover 100 illustrating the inner and outer cover members assembled with one another.

As shown, the outer cover member 102 generally includes proximal end 106, a distal end 108, which includes a handle or grip 110 allowing for rotation of the outer cover member 102 relative to the inner cover member 104 when a user wishes to transition the cover 100 from a first configuration, in which the needle of the delivery device may be accessed, to second configuration, which essentially locks the outer and inner cover members 102, 104 to one another, as will be described in greater detail herein.

The outer cover member 102 further includes an opening 112 extending along a length thereof. The opening 112 is configured to allow a needle to pass therethrough when the cover 100 bends along a hinge, as will be described herein. For example, as shown, the opening 112 extends a length from the proximal end 106 towards the distal end 108 that generally corresponds to a length of the needle extending within the cover members. The outer cover member 102 further includes a breakaway tab member 114 positioned within the opening 112 of the outer cover member 102. The breakaway tab member 114 has perforations, scores, or other cut-outs along the sides 115 where the tab member 114 is coupled to the opening 112.

Accordingly, the tab member 114 serves at least two purposes: 1) it is a safety feature in that the tab member 114 is a breakaway tab (able to be torn free from the opening 112), which indicates whether the cover 100 has been used or not and thus whether the needle is safe for use; and 2) it prevents the opening 112 from collapsing during manufacture (i.e., the tab 114 helps keep index of the outer cover member 102 and the opening 112 during the molding process). The outer cover member 102 further includes at least a first aperture 116 configured to receive corresponding first and second protrusions formed the inner cover member 104, as will be discussed herein.

Figure 16:
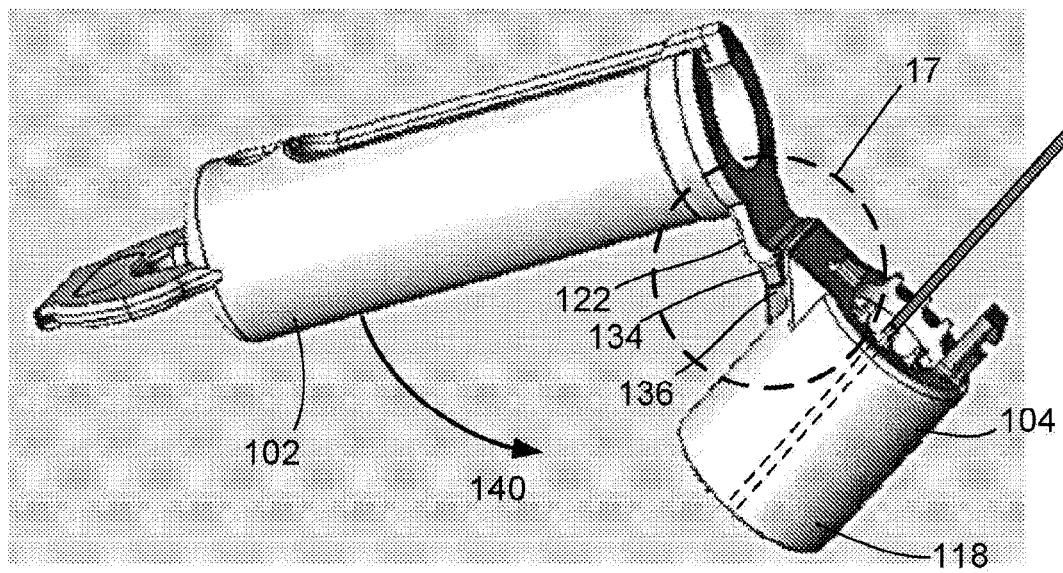
FIG. 16 is a perspective view of the safety needle cover of FIG. 11 in an open position and exposing the needle for delivery of a therapeutic agent.
Figure 17:
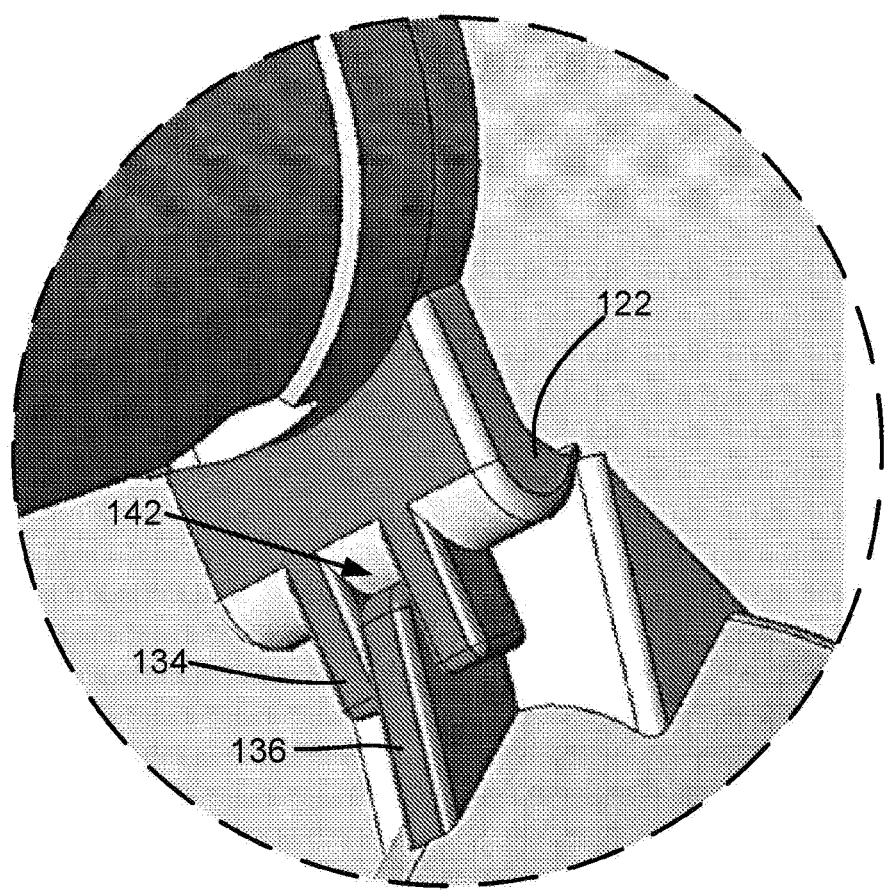
FIG. 17 is an enlarged perspective view of hinge member and corresponding stopping members engaging one another when the safety needle cover is in a fully open position.

The inner cover member 104 includes a proximal portion 118 and a distal portion 120, which are generally separated by a hinge member 122. The hinge member 122 is a living hinge, thereby allowing for repeated movement between a closed configuration (as shown when the outer and inner cover members 102, 104 are closed over the needle) and an open configuration (as shown in FIGS. 16 and 17 when the outer cover member 102 and a portion of the inner cover member 104 (e.g., distal portion 120) are bent out of plane with the needle to allow for needle use). In some embodiments, the hinge member 122 may be molded in such a manner so that the default shape is in the closed configuration such that the hinge member 122 has shape memory to cause the outer cover member 102 and portion of the inner cover member 104 to return to the default shape so as to cause the needle to be covered. In some embodiments, the hinge member 122 may include a shape memory material. Yet still, in some embodiments, the hinge member 122 may include features that limit, or otherwise prevent, the cover from over rotating when a user is opening the cover, as will be described in greater detail herein. It should be noted that the proximal and distal portions 118, 120 of the inner cover member 104 are further coupled to one another in a breakaway fashion. In particular, the connection 123 between the proximal and distal portions 118, 120 includes perforations, scores, or other cut-outs, thereby allowing for the distal portion 120 of the inner cover member 104 to break away from the proximal portion 118 when a user moves the cover from the closed position to the open position. The connection 123 serves at least two purposes: 1) it is a safety feature in that the perforated or scored connection 123 serves as a breakaway connection, which indicates whether the cover 100 has been used or not and thus whether the needle is safe for use; and 2) it prevents the proximal portion 118 and distal portion 120 from collapsing during manufacture (i.e., the connection 123 helps keep index of the inner cover member 104 throughout its length during the molding process).

Figure 15A:
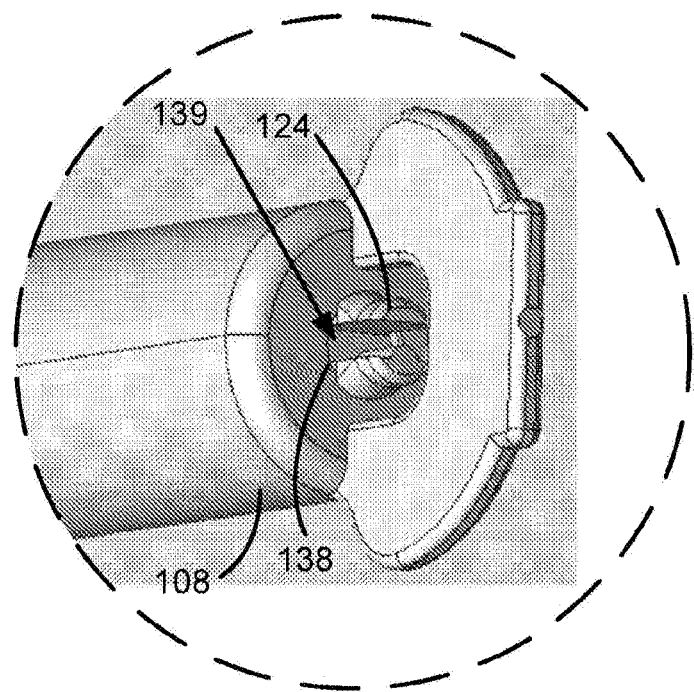
FIG. 15A is an enlarged perspective view of the distal end of the outer cover member illustrating coupling of the inner and outer cover members via engagement between a pin on the distal end of the inner cover member and a bore defined on the distal end of the outer cover member.

The inner cover member 104 further includes a pin 124 extending from the distal portion 120, wherein the pin 124 is configured to be received and retained within a corresponding bore 138 in the distal end 108 of the outer cover member 102 (as shown in FIG. 15A) and further allow the inner and outer cover members to be rotatably coupled to one another about a longitudinal axis of the pin 124. The inner cover member 104 further includes an opening 126 extending along a length thereof. The opening 126 is similarly configured as the opening 112 of the outer cover member 102. For example, as shown, the opening 126 extends a length from the proximal end 118 towards the distal end 120 that generally corresponds to a length of the needle extending within the cover members and further resembles the opening 112 of the outer cover member 102. Accordingly, when the openings 112, 126 of the outer and inner cover members 102, 104 are aligned with one another, the openings 112, 126 are configured to allow a needle to pass therethrough when the cover 100 bends along the hinge 122. The inner cover member 104 further includes a first protrusion 128 and a second protrusion 132, each extending from an exterior surface on opposing sides of the inner cover member 104, generally closer to the distal portion 120 than the proximal portion 118. The inner cover member 104 further includes a third protrusion 129 extending from an exterior surface of a side of the inner cover member 104 and generally closer to the proximal portion 118 than the distal portion 120. In particular, the third protrusion 129 may be located on the same said of the inner cover member 104 as the second protrusion 132, such that the second protrusion 132 is positioned closer to the distal portion 120 while the third protrusion 129 is positioned closer to the proximal portion 118 and adjacent to the hinge member 122.

As will be described in greater detail herein, the first and second protrusions 128, 132 are configured to be received within the first aperture 116 of the outer cover member 102 when the cover 100 is in the first configuration and the second configuration, respectively. In particular, the first aperture 116 is defined generally at or near the distal end 108 of the outer cover member 102 and generally in alignment with the first and second protrusions 128, 132 when the inner and outer cover members are assembled with one another, such that rotation of the outer cover member 102 relative to the inner cover member 104 results in engagement between the first aperture 116 and one of the first and second protrusions 128, 132. The outer cover member 102 further includes a second aperture 130, generally defined at or near the proximal end 106 of the outer cover member 102 and in general alignment with the third protrusion 129 when the inner and outer cover members are assembled with one another, such that rotation of the outer cover member 102 relative to the inner cover member 104 results in engagement between the second aperture 130 and the third protrusion 129. The first, second, and third protrusions 128, 132, 129 allow for the cover 100 to be placed in two different configurations, as described below and illustrated in FIGS. 18A-21.

FIG. 15A is an enlarged perspective view of the distal end 108 of the outer cover member 102 illustrating coupling of the inner and outer cover members via engagement between a pin 124 on the distal end 120 of the inner cover member 104 and a bore 138 defined on the distal end 108 of the outer cover member 102. As shown, the bore 138 is sealed by way of a solid pin design (i.e., there is no exposure of the inner cavity formed by the assembly of the inner and outer cover members with one another), which may further prevent the spread of disease from a used needle by containing the fluid and biological matter within the locked cover 100.

Figure 15B:
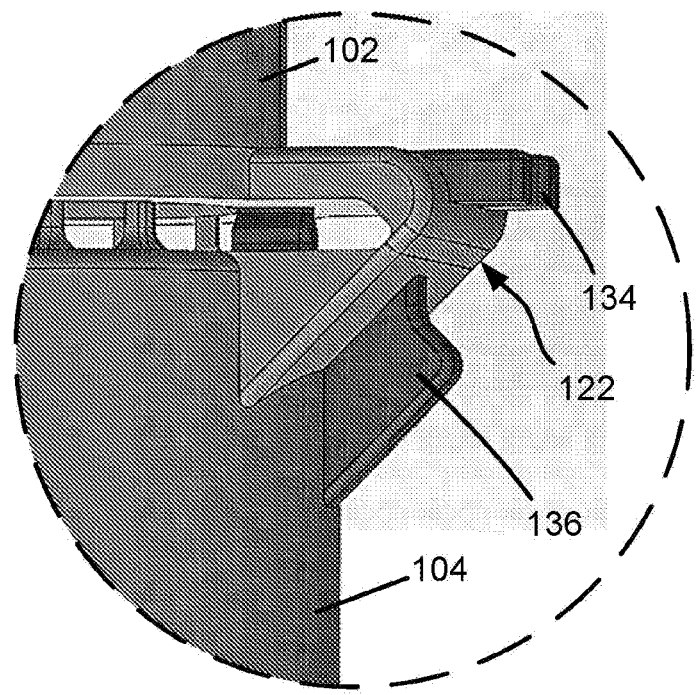
FIG. 15B is an enlarged perspective view of the hinge member coupling the proximal and distal portions of the inner cover member to one another.

As previously described, the hinge member 122 may include features for preventing over rotation of the cover 100 when a user is opening the cover to use the delivery device (i.e., to administer therapeutic agent via needle injection). For example, FIG. 15B is an enlarged perspective view of the hinge member 122 coupling the proximal portion 118 and distal portion 120 of the inner cover member 104 to one another. FIG. 15B illustrates the corresponding stopping members 134, 136 formed on opposing ends of the hinge member 122 and configured to prevent over extension of the cover when transitioning from the closed position to the open position. In particular, a first stopping member 134 formed on a first end of the hinge member 122 may include two extensions having a slot formed there between and the second stopping member 136, formed on an opposing end of the hinge member 122, may be a single extension configured to be received within the slot of the first stopping member 134. When the cover transitions to an open position, as indicated by arrow 140 in FIG. 16, the corresponding stopping members 134 and 136 engage one another, as indicated by arrow 142 in FIG. 17, to thereby prevent the cover from over rotating and potentially damaging the cover.

Figure 21:
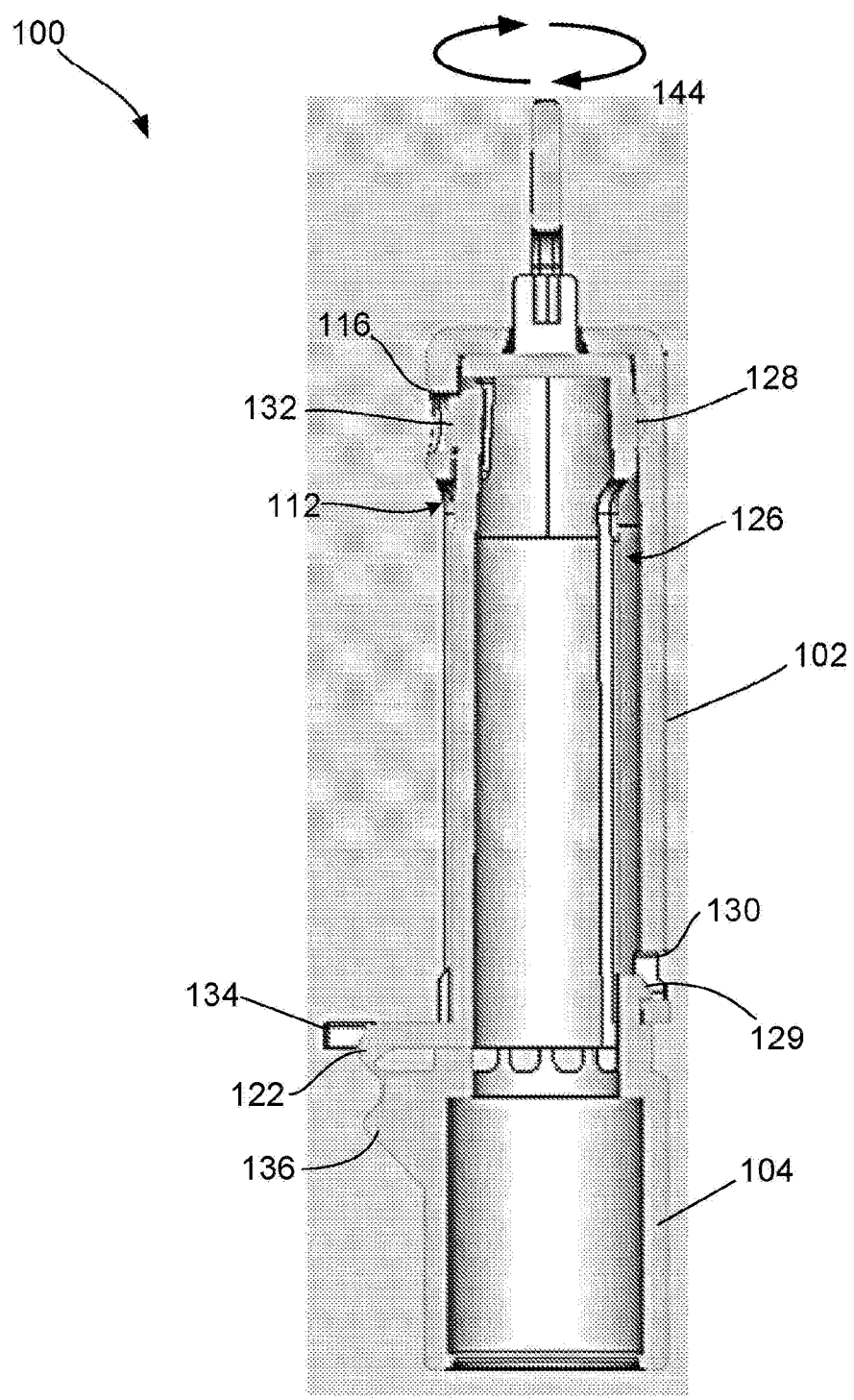
FIG. 21 is a sectional view of the safety needle cover taken along lines C-C in FIG. 20A.

FIGS. 18A and 18B are front and rear views of the safety needle cover 100 in the first configuration and having the tab member 114 intact, ready for use of the delivery device (i.e., administration of a therapeutic agent via needle injection). FIG. 19 is a sectional view of the safety needle cover 100 taken along lines B-B in FIG. 18A. FIGS. 20A and 20B are front and rear views of the safety needle cover 100 transitioned from the first configuration into the second configuration in which the cover 100 is permanently locked and the needle is enclosed within. FIG. 21 is a sectional view of the safety needle cover taken along lines C-C in FIG. 20A.

Figure 18:
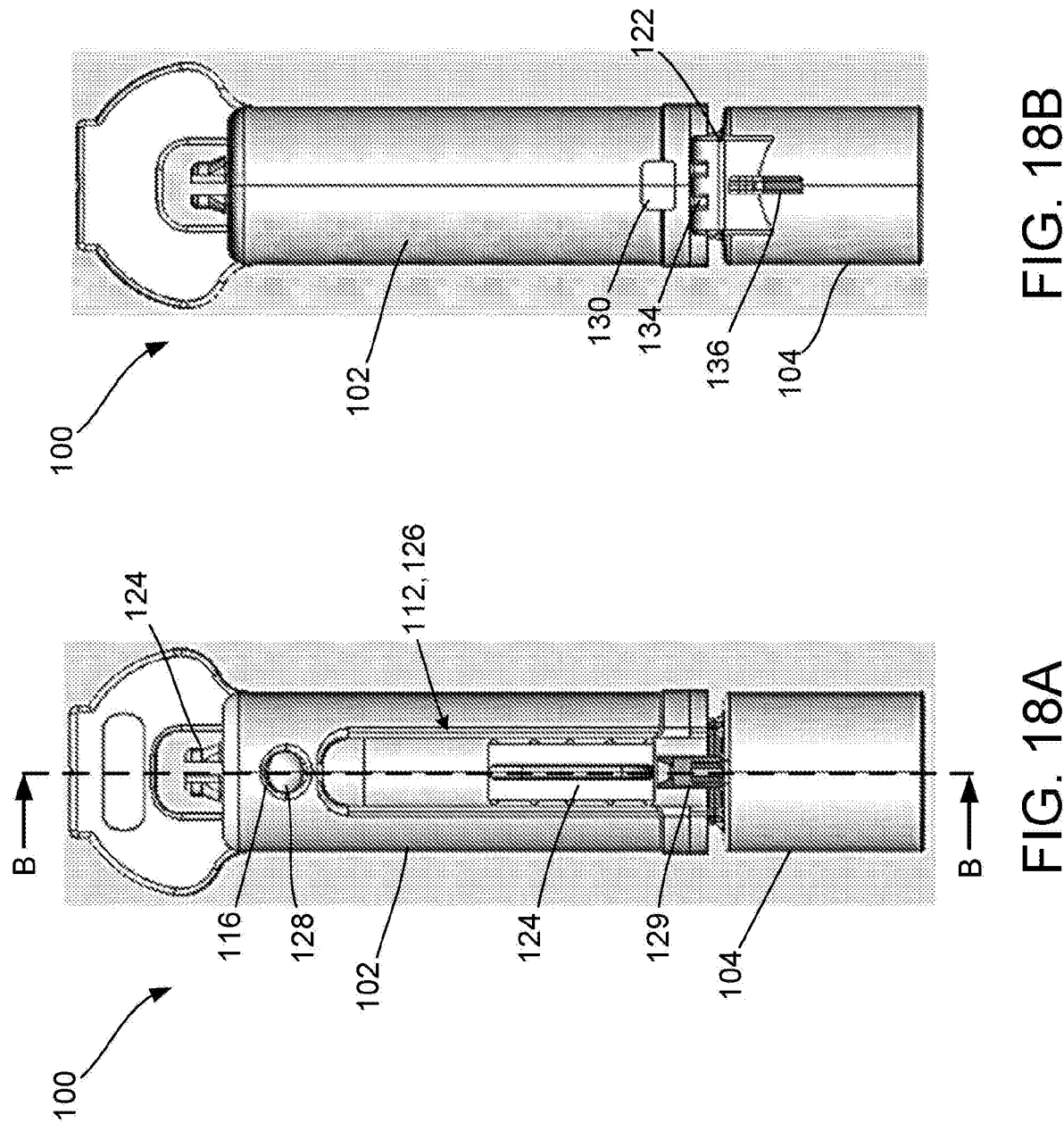
FIGS. 18A and 18B are front and rear views of the safety needle cover of FIG. 11 in the first configuration and having the tab member intact, ready for use of the delivery device (i.e., administration of a therapeutic agent via needle injection).
Figure 19:
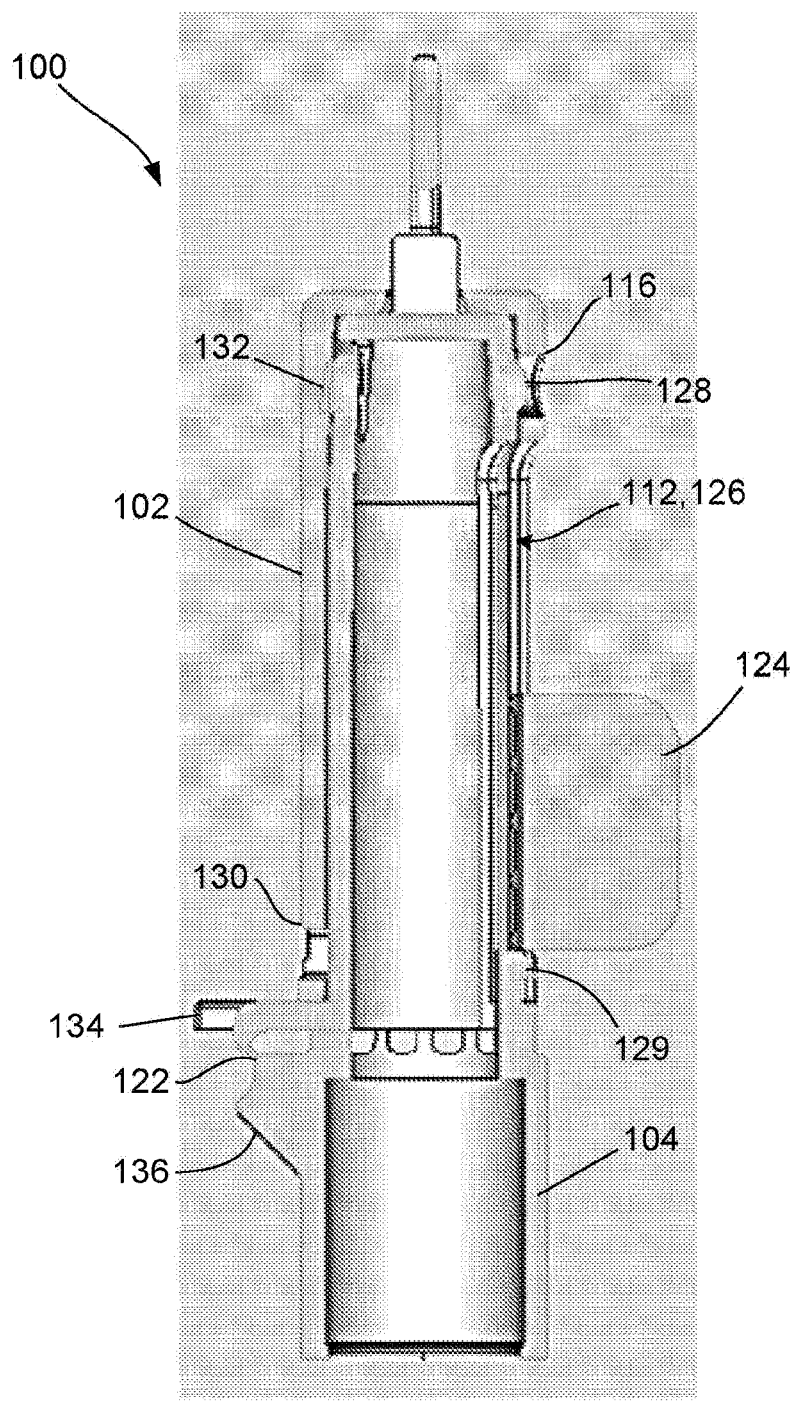
FIG. 19 is a sectional view of the safety needle cover taken along lines B-B in FIG. 18A.
Figure 20:
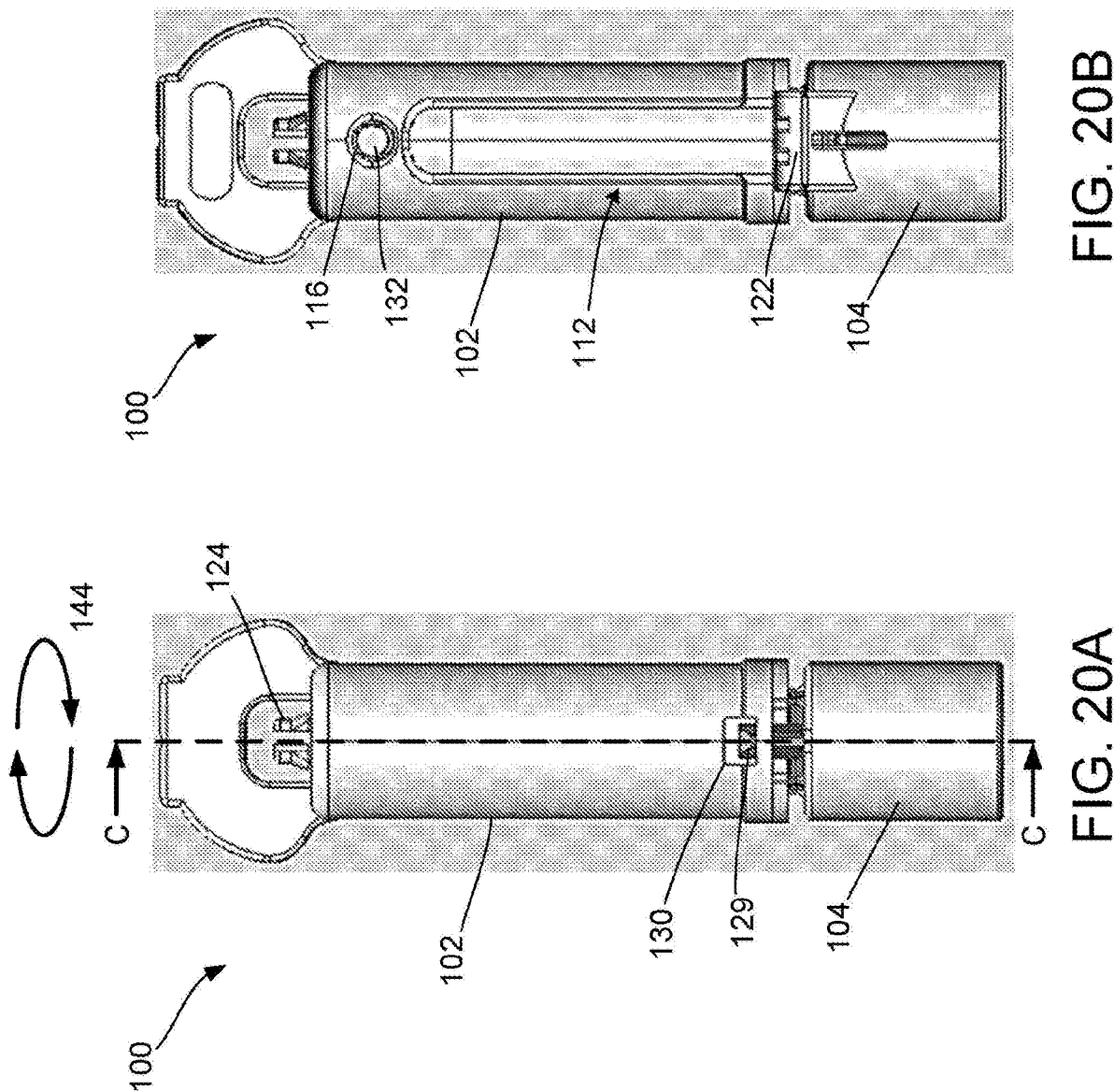
FIGS. 20A and 20B are front and rear views of the safety needle cover of FIG. 11 transitioned from the first configuration into the second configuration in which the cover is permanently locked and the needle is enclosed within.

The safety needle cover 100 comprises at least a first configuration shown in FIGS. 18 A, 18B, and 19, in which a user can manipulate the cover in such a manner so as to gain access to the needle (i.e., expose the needle) for administering a therapeutic agent. For example, as previously described, the outer cover member 102 and the inner cover member 104 each have an opening 11, 126, respectively, extending along a longitudinal length thereof, generally in alignment with a length of the needle when the cover is in the first configuration. The inner and outer cover members are rotatably coupled to one another (via engagement between pin 124 of the inner cover member 104 and the bore 138 of the outer cover member 102) so as to allow each cover member to rotate relative to one another while remaining coupled to one another. The inner cover member 104 includes a first protrusion 128 extending from an exterior surface on one side of the inner cover member 104 and the outer cover member 102 includes a corresponding aperture or recess 116 configured to receive the first protrusion 128 therein. When in the first configuration, the first protrusion 128 of the inner cover member 104 is engaging and positioned within the aperture 116 of the outer cover member 102, thereby preventing the inner and outer cover members from freely rotating relative to one another and further ensuring that the openings of each of the inner and outer cover members are aligned with one another. When a user is ready to expose the needle so as to administer a therapeutic agent via injection, the user need only remove the breakaway tab 114 and apply sufficient application of force to the safety needle cover 100, specifically at the distal portion 108 of the outer cover member 102, at which point the perforated connection 123 will break away and the assembled inner and outer cover members will to bend relative to the proximal portion 118 of the inner cover member 104 at the hinge 122, as previously shown in FIG. 16. As the assembly inner and outer cover members bend, the needle is exposed and able to pass through the aligned openings of the inner and outer cover members as the inner and outer cover members are displaced to the side.

Upon administering the therapeutic agent, a user need only bend the assembled inner and outer cover members to a closed position over the needle. In the event that the delivery device is intended for single use only, a user can than then further manipulate the cover so as to permanently enclose the needle within to prevent subsequent access to the needle, thereby preventing the risk of re-use of the needle and inadvertent needlestick. For example, as shown in FIGS. 20A, 20B, and 21, the safety needle cover 100 comprises a second configuration in which a user can manipulate the cover in such a manner so as to permanently enclose the needle by simply twisting the inner and outer cover members relative to one another until the second protrusion 132 of the inner cover member 104 engages the first aperture 116 of the outer cover member 102. The second protrusion 132 extends from an exterior surface of a side of the inner cover member 104 that is generally opposite the first protrusion 128 (i.e., approximately 180 degrees). Accordingly, a user need only twist the outer cover member 102 half of a full rotation (i.e., 180 degrees) about the longitudinal axis X, as indicated by arrow 144, to set the second protrusion 132 of the inner cover member 104 within the aperture 116 of the outer cover member 102.

It should be noted that the first protrusion 128 is constructed in such a manner so as to sufficiently engage the first aperture 116 of the outer cover member 102 to prevent free rotation of the inner and outer cover members relative to one another but has a relatively shallow profile which will allow the first protrusion 128B to disengage from the first aperture 116 of the outer cover member 102 upon application of sufficient torque to the outer cover member 102.

Accordingly, a user need only rotate the outer cover member 102 approximately a half rotation, at which point, the second protrusion 132 will engage and be received within the first aperture 116. Similarly, upon twisting the outer cover member 102 a half rotation, the third protrusion 129 of the inner cover member 104 will engage and lock into the second aperture 130 of the outer cover member 102. Unlike the first protrusion 128, however, the second and third protrusions 132, 129 may include a biasing member for applying a biasing force in an outward direction (i.e., away from the inner cover member 104 and towards the outer cover member 102), thereby locking the second and third protrusions 132, 129 within the first and second apertures 116, 130, respectively, and preventing disengagement even when a user attempts to twist the outer cover member 102. When the second and third protrusions 132, 129 are in engagement with the first and second apertures 116, 130, the opening 112 of the outer cover member 102 is no longer aligned with the corresponding opening 126 of the inner cover member 104. Rather, the openings 122, 126 are substantially opposing one another on opposing sides of the cover, thereby effectively creating a complete enclosure of the needle within the inner and outer cover members.

Another embodiment of a safety needle cover 200 consistent with the present disclosure is illustrated in FIGS. 22-27. The safety needle cover 200 may include similar features and components or parts of the safety needle covers 10 and 100 of FIGS. 1-10 and 11-21, respectively, and previously described herein. Accordingly, like parts may have similar reference numerals.

Figure 22:
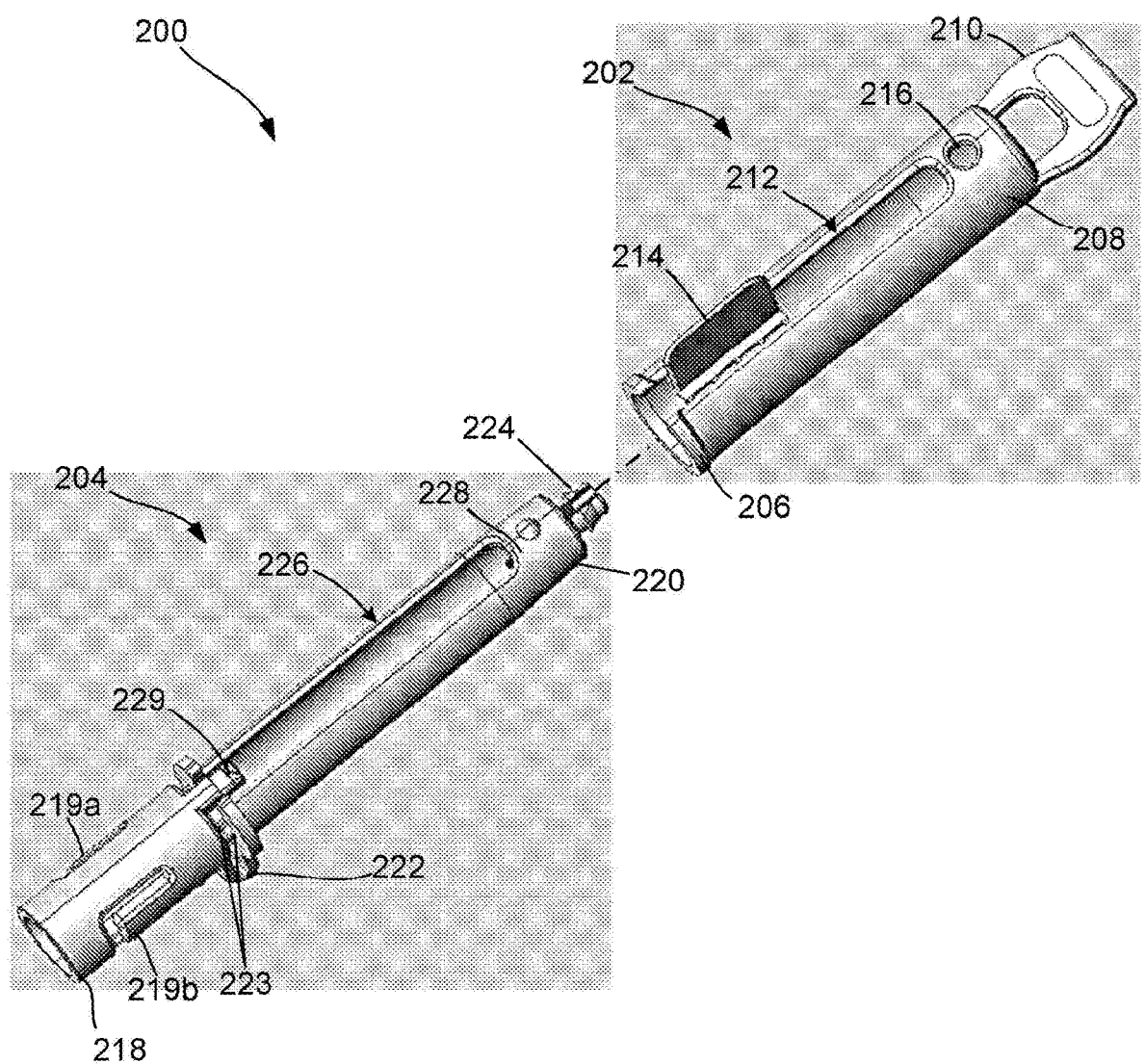
FIG. 22 is a front perspective exploded view of another embodiment of a safety needle cover consistent with the present disclosure illustrating inner and outer cover members separated from one another.

FIG. 22 is a front perspective exploded view a safety needle cover 200 consistent with the present disclosure. The safety needle cover 200 is a relatively simple design comprising two cover members, an outer cover member 202 and an inner cover member 204 coupled to one another in a concentric manner. In particular, the outer cover member 202 includes a cavity shaped and sized to receive a majority of the inner cover member 204 within. The inner cover member 204 also includes a cavity configured to enclose a needle extending from a delivery device to which the safety needle cover is directly coupled to.

As shown, the outer cover member 202 generally includes proximal end 206, a distal end 208, which includes a handle or grip 210 allowing for rotation of the outer cover member 202 relative to the inner cover member 204 when a user wishes to transition the cover 200 from a first configuration, in which the needle of the delivery device may be accessed, to second configuration, which essentially locks the outer and inner cover members 202, 204 to one another, as will be described in greater detail herein. The outer cover member 202 further includes an opening 212 extending along a length thereof. The opening 212 is configured to allow a needle to pass therethrough when the cover 200 bends along a hinge, as will be described herein. For example, as shown, the opening 212 extends a length from the proximal end 206 towards the distal end 208 that generally corresponds to a length of the needle extending within the cover members. The outer cover member 202 further includes a breakaway tab member 214 positioned within the opening 212 of the outer cover member 202. Accordingly, the tab member 114 serves at least two purposes: 1) it is a safety feature in that the tab member 214 is a breakaway tab (able to be torn free from the opening 212), which indicates whether the cover 200 has been used or not and thus whether the needle is safe for use; and 2) it prevents the opening 212 from collapsing during manufacture (i.e., the tab 214 helps keep index of the outer cover member 202 and the opening 212 during the molding process). The outer cover member 202 further includes at least a first aperture 216 configured to receive corresponding first and second protrusions formed the inner cover member 204, as will be discussed herein.

The inner cover member 204 includes a proximal portion 218 and a distal portion 220, which are generally separated by a hinge member 222. The hinge member 222 is a living hinge, thereby allowing for repeated movement between a closed configuration (as shown when the outer and inner cover members 202, 204 are closed over the needle) and an open configuration.

It should be noted that the proximal and distal portions 218, 220 of the inner cover member 204 are further coupled to one another in a breakaway fashion. In particular, the connection 223 between the proximal and distal portions 218, 220 includes perforations, scores, or other cut-outs, thereby allowing for the distal portion 220 of the inner cover member 204 to break away from the proximal portion 218 when a user moves the cover from the closed position to the open position. The connection 223 serves at least two purposes: 1) it is a safety feature in that the perforated or scored connection 223 serves as a breakaway connection, which indicates whether the cover 200 has been used or not and thus whether the needle is safe for use; and 2) it prevents the proximal portion 218 and distal portion 220 from collapsing during manufacture (i.e., the connection 223 helps keep index of the inner cover member 204 throughout its length during the molding process).

The inner cover member 204 further includes a pin 224 extending from the distal portion 220, wherein the pin 224 is configured to be received and retained within a corresponding bore (not shown) n the distal end 208 of the outer cover member 202 (in a similar design as shown in FIG. 15 A) and further allow the inner and outer cover members to be rotatably coupled to one another about a longitudinal axis of the pin 224. The inner cover member 204 further includes an opening 226 extending along a length thereof. The opening 226 is similarly configured as the opening 212 of the outer cover member 202. For example, as shown, the opening 226 extends a length from the proximal end 218 towards the distal end 220 that generally corresponds to a length of the needle extending within the cover members and further resembles the opening 212 of the outer cover member 202. Accordingly, when the openings 212, 226 of the outer and inner cover members 202, 204 are aligned with one another, the openings 212, 226 are configured to allow a needle to pass therethrough when the cover 200 bends along the hinge 222.

The inner cover member 204 further includes a first protrusion 228 and a second protrusion (not shown), each extending from an exterior surface on opposing sides of the inner cover member 204, generally closer to the distal portion 220 than the proximal portion 218. The inner cover member 204 further includes a third protrusion 229 extending from an exterior surface of a side of the inner cover member 204 and generally closer to the proximal portion 218 than the distal portion 220. In particular, the third protrusion 229 may be located on the same said of the inner cover member 204 as the second protrusion (not shown), such that the second protrusion is positioned closer to the distal portion 220 while the third protrusion 229 is positioned closer to the proximal portion 218 and adjacent to the hinge member 222.

As previously described herein, the first and second protrusions are configured to be received within the first aperture 216 of the outer cover member 202 when the cover 200 is in the first configuration and the second configuration, respectively. In particular, the first aperture 216 is defined generally at or near the distal end 208 of the outer cover member 202 and generally in alignment with the first and second protrusions when the inner and outer cover members are assembled with one another, such that rotation of the outer cover member 202 relative to the inner cover member 204 results in engagement between the first aperture 216 and one of the first and second protrusions. The outer cover member 202 further includes a second aperture (not shown), generally defined at or near the proximal end 206 of the outer cover member 202 and in general alignment with the third protrusion 229 when the inner and outer cover members are assembled with one another, such that rotation of the outer cover member 202 relative to the inner cover member 204 results in engagement between the second aperture and the third protrusion 229. The first, second, and third protrusions allow for the cover 200 to be placed in two different configurations, as previously described herein and shown in FIGS. 18A-21.

Figure 23:
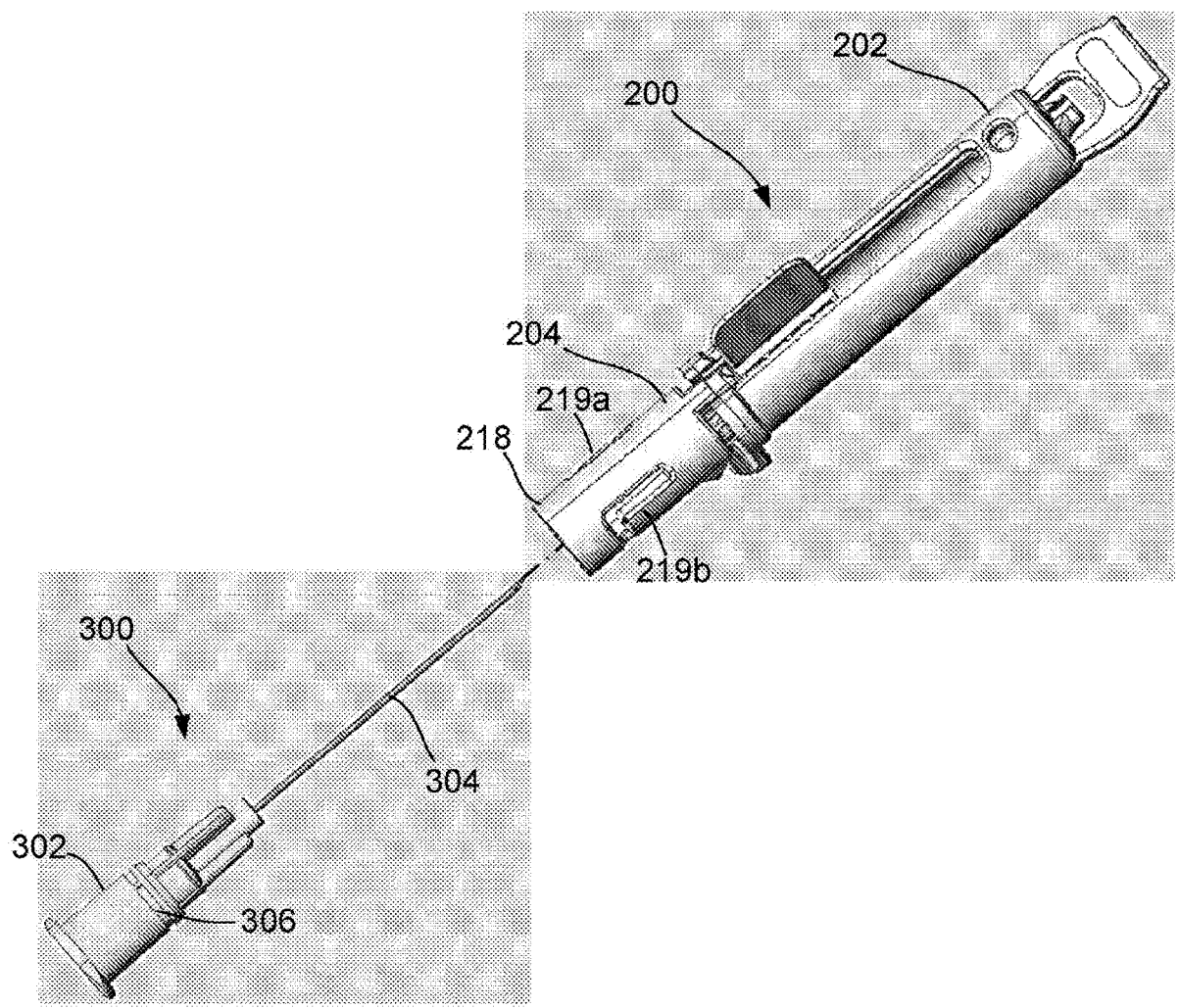
FIG. 23 is a front perspective view of the safety needle cover of FIG. 22 in an assembled configuration and further illustrating an exemplary hub of a delivery device or assembly to which the safety needle cover is configured to be directly coupled thereto.

FIG. 23 is a front perspective view of the safety needle cover 200 in an assembled configuration and further illustrating a hub portion 300 of an exemplary delivery device to which the safety needle cover 200 is configured to be directly coupled thereto. As shown, the hub 300 includes a body having a proximal end and a distal end to which a needle 304 is coupled and extending therefrom. The hub 300 may generally resemble a standard ISO-style hub, which includes a standard Luer-Lok fitting at the proximal end and configured to be coupled to a source (e.g., syringe or vial) containing a fluid agent to be delivered, via the needle or other administration means (e.g., nozzle), to a patient. The hub 300 may further include a connection fitting to which the cover 200 may be coupled. For example, as shown, the hub body 302 may have an undercut 306 extending around a perimeter thereof. The cover 200, specifically the inner cover member 204 further includes snap-fitting hook members 219a and 219b formed on the proximal portion 218. For example, the snap-fitting hook members 219a and 219b may be positioned on opposing sides of the inner cover member 204, generally opposing one another. Each of the snap-fitting hook members 219a, 219b is configured to engage the corresponding undercut 306 of the hub 302 upon sliding of the cover 200 onto the hub 300, as shown in FIGS. 24-27. It should be noted that the hub 300 may also generally resemble non-standard, non-ISO-style hubs which may include non-standard connection fittings.

Figure 24:
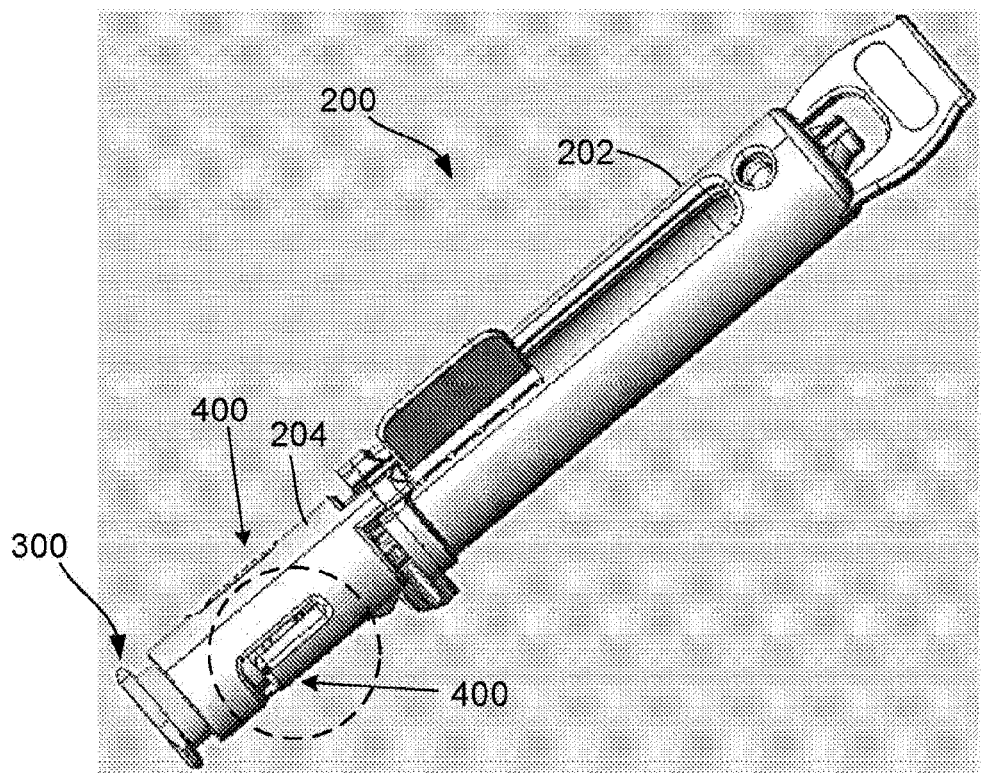
FIG. 24 is a front perspective view of the safety needle cover securely coupled to the hub.
Figure 25:
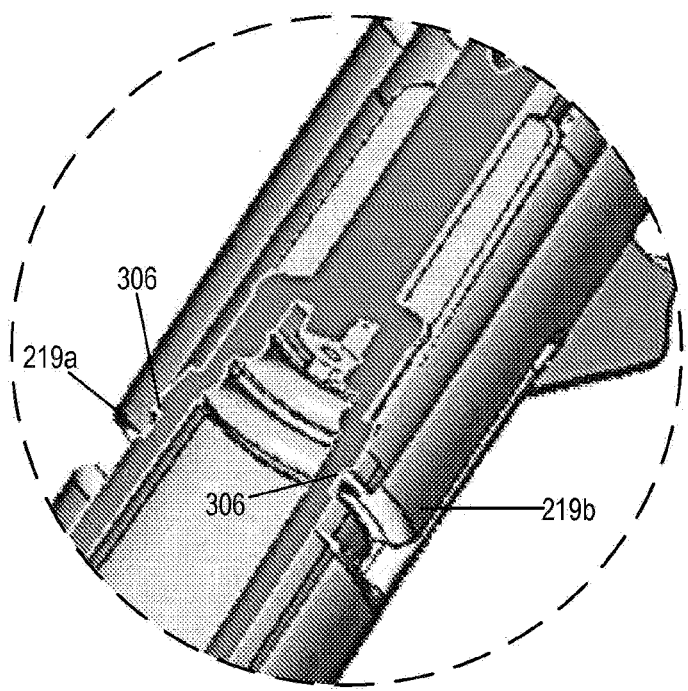
FIG. 25 is an enlarged perspective sectional view of the safety needle cover securely coupled to the hub illustrating engagement between the snap-fitting hook members of the inner cover member engaging corresponding undercuts defined on the body of the hub.
Figure 27:
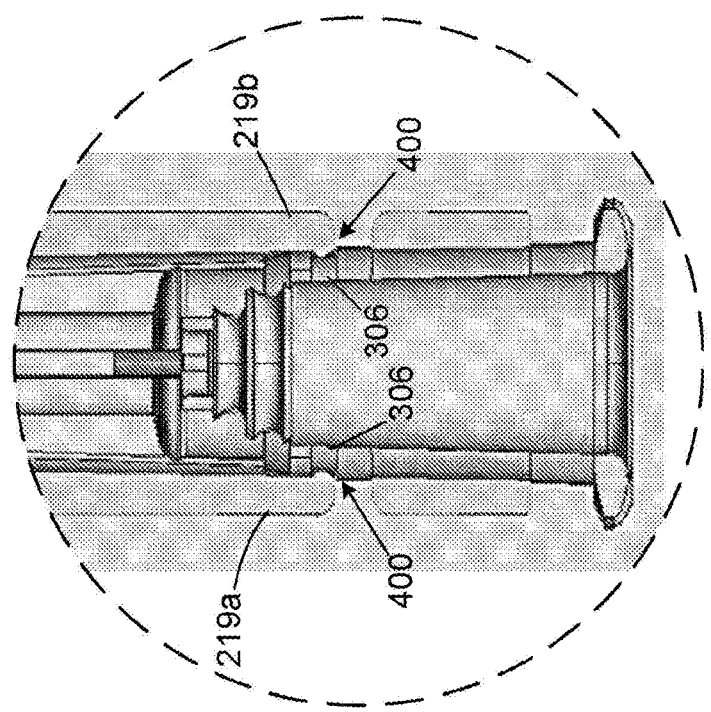
FIG. 27 is an enlarged side sectional view of the safety needle cover securely coupled to the hub taken along lines D-D in FIG. 26 and illustrating engagement between the snap-fitting hook members of the inner cover member engaging corresponding undercuts defined on the body of the hub.
Figure 26:
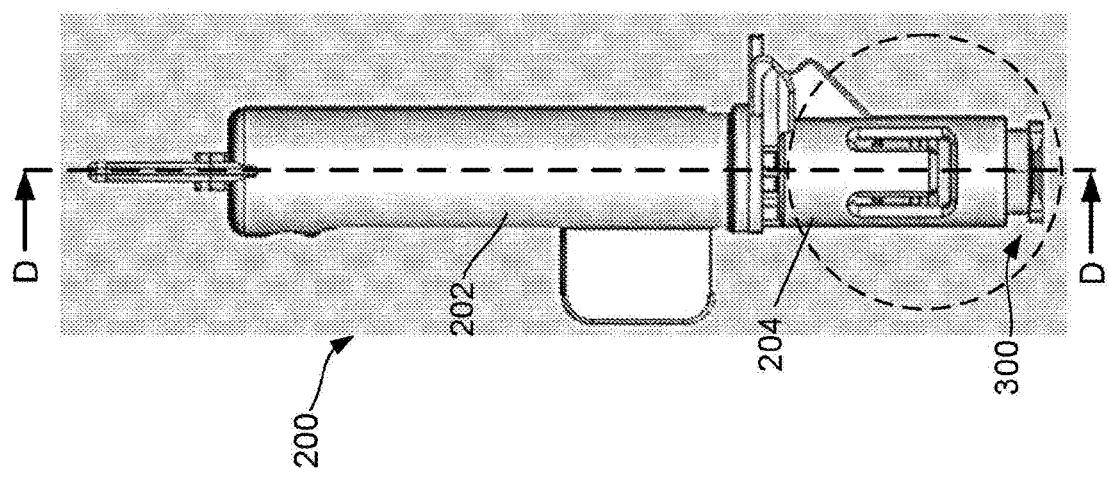
FIG. 26 is a side view of the safety needle cover securely coupled to the hub.

FIG. 24 is a front perspective view of the safety needle cover 200 securely coupled to the hub 300. FIG. 25 is an enlarged perspective sectional view of the safety needle cover 200 securely coupled to the hub 300. FIG. 26 is side view of the safety needle cover 200 securely coupled to the hub 300. FIG. 27 is an enlarged side sectional view of the safety needle cover 200 securely coupled to the hub 300 taken along lines D-D in FIG. 26. FIGS. 25 and 27 illustrate engagement between the snap-fitting hook members 219a, 219b of the inner cover member 204 with the corresponding undercut 306 defined on the body 302 of the hub 300, as indicated by arrows 400. The engagement between the snap-fitting hook members and the undercut may generally provide a secure engagement between the cover 200 and the hub 300 and make it difficult to remove the cover 200 from the hub 300, thereby increasing safety and preventing unwanted needle stick. Another embodiment of a safety needle cover 500 consistent with the present disclosure is illustrated in FIGS. 28, 29, 30, 31, 32, 33, 34A, 34B, 34C, 35A, and 35B. The safety needle cover 500 may include similar features and components or parts of the safety needle covers 10, 100, and 200 of FIGS. 1-10, 11-21, and 22-28, respectively, and previously described herein. Accordingly, like parts may have similar reference numerals.

Figure 28:
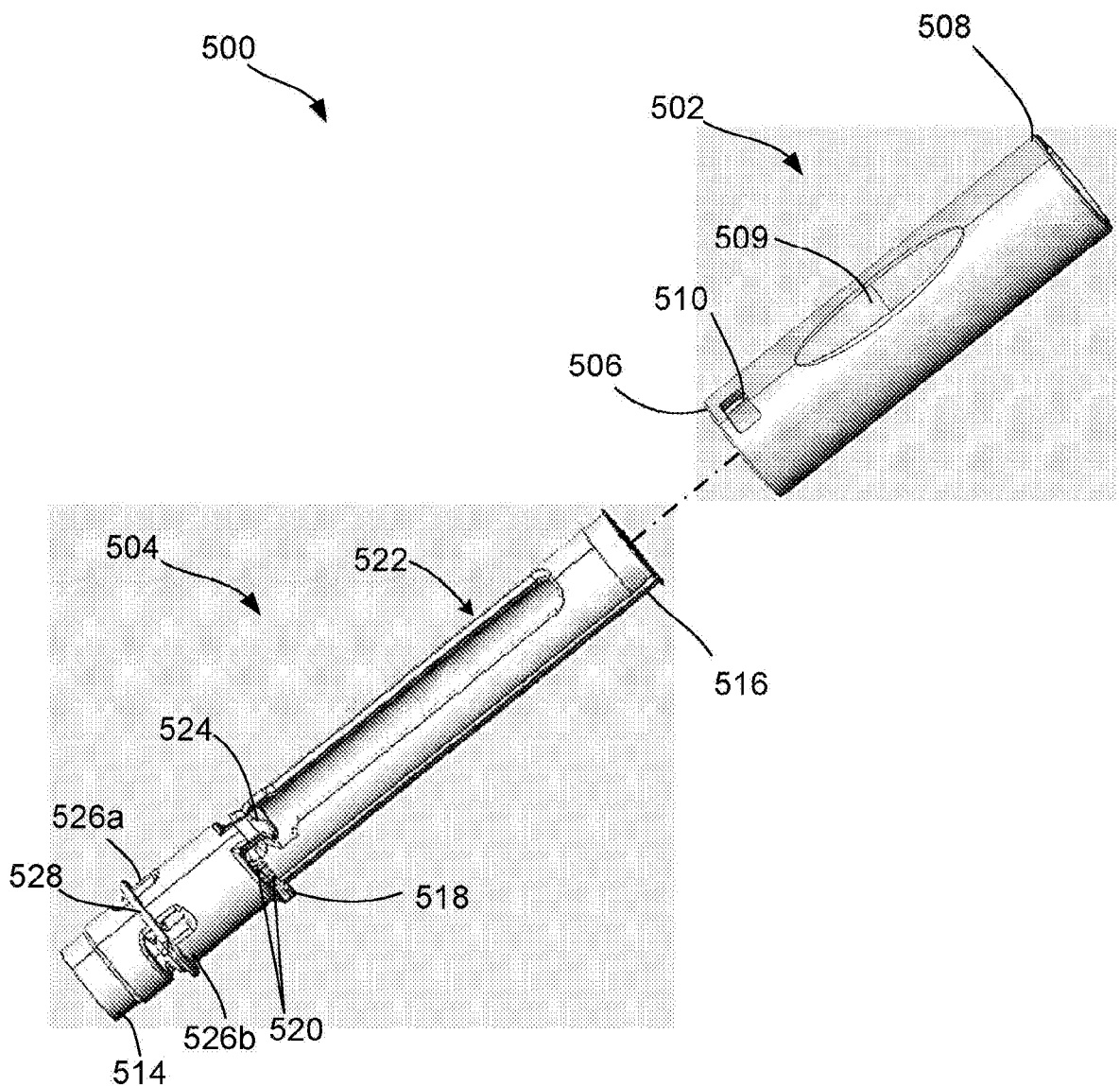
FIG. 28 is a front perspective exploded view of another embodiment of a safety needle cover consistent with the present disclosure illustrating inner and outer cover members separated from one another.
Figure 29:
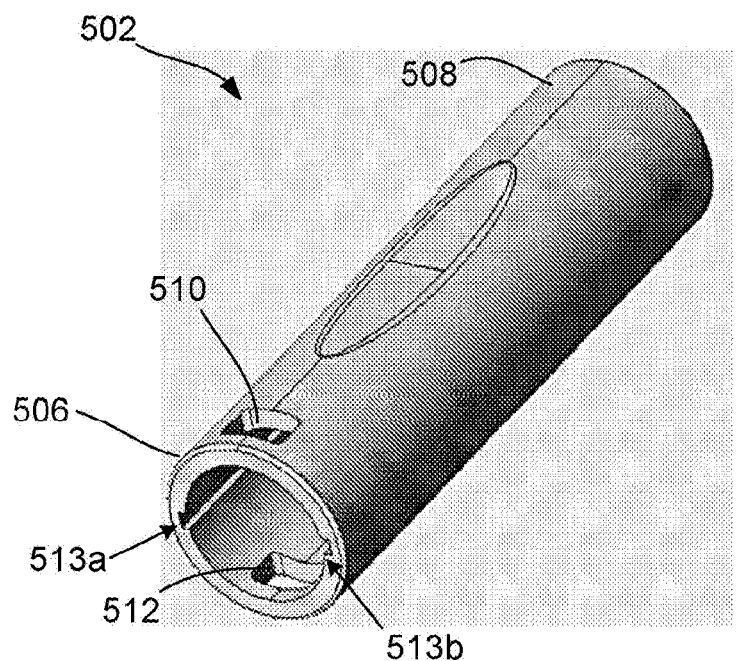
FIG. 29 is a front perspective view of the outer cover member.
Figure 30:
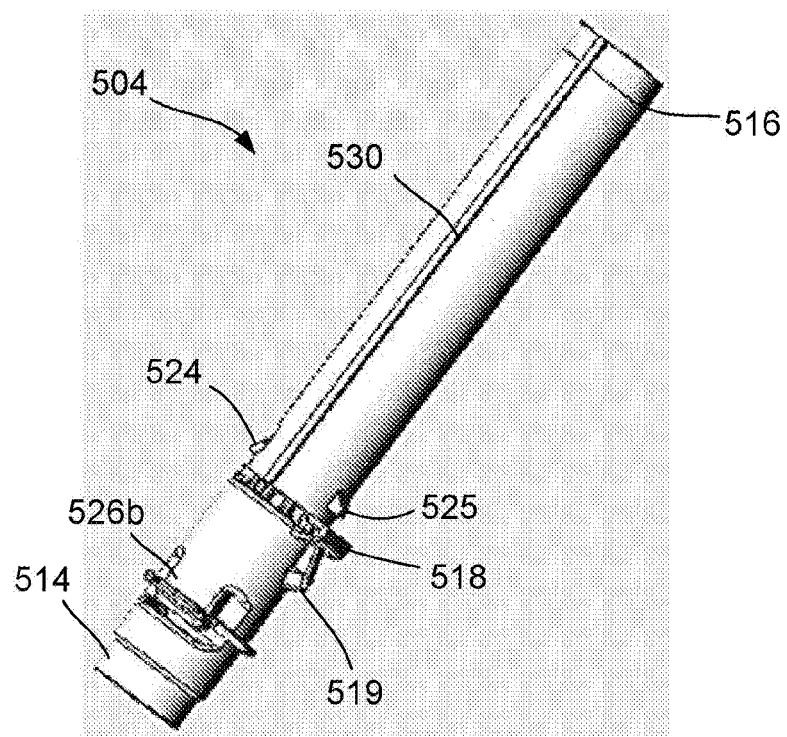
FIG. 30 is a rear perspective view of the inner cover member.
Figure 32:
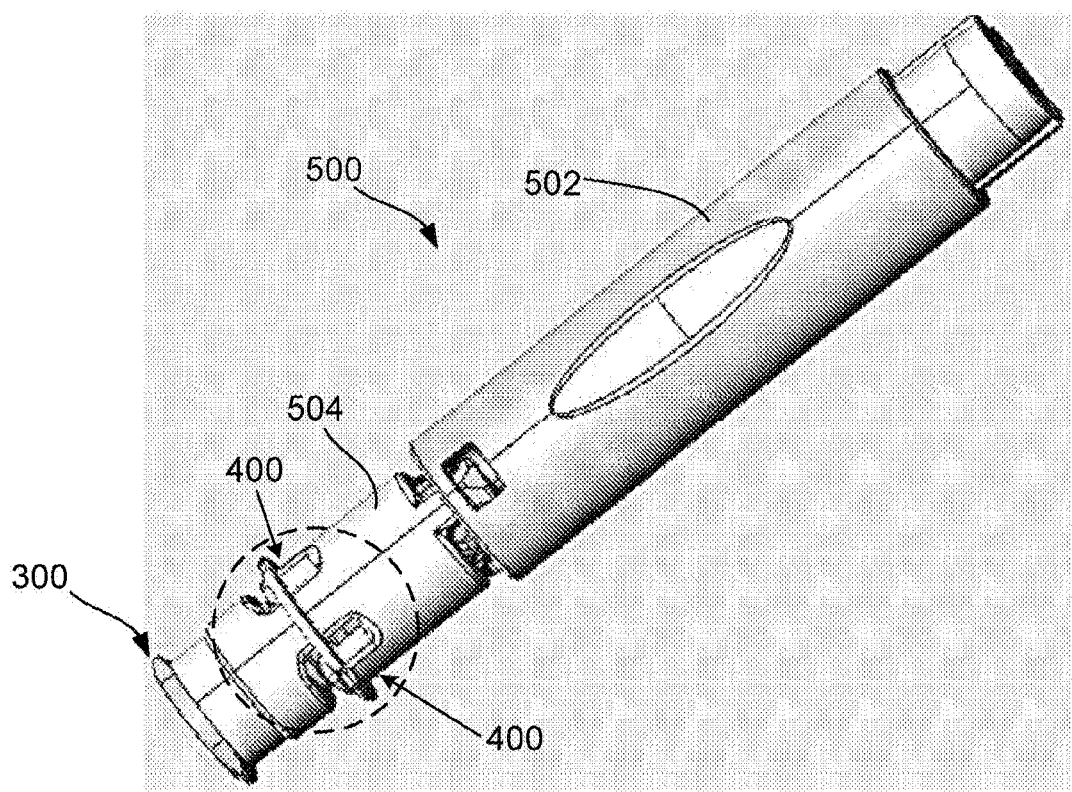
FIG. 32 is a front perspective view of the safety needle cover securely coupled to the hub.

FIG. 28 is a front perspective exploded view of a safety needle cover 500 having a relatively simple design comprising two cover members, an outer cover member 502 and an inner cover member 504 coupled to one another in a concentric manner. FIGS. 29 and 30 are front and rear perspective views of the outer and inner cover members 502, 504, respectively. The outer cover member 502 includes a cavity shaped and sized to receive a majority of the inner cover member 504 within. The inner cover member 504 also includes a cavity configured to enclose a needle extending from a delivery device to which the safety needle cover 500 is directly coupled to, as shown in FIG. 32, for example.

As shown, the outer cover member 502 generally includes proximal end 506, a distal end 508, and a grip portion 509 defined along the body of the outer cover member between the proximal and distal ends 506, 508. The grip portion 509 provides an area for a user to grip and move the outer cover member 502 relative to the inner cover member 504 when a user wishes to transition the cover 500 from an unlocked configuration, in which the outer and inner cover members 502, 504 are unlocked from one another and the needle of the delivery device may be accessed, to a locked configuration, in which the outer and inner cover members 502, 504 are essentially locked to one another thereby preventing access to the needle of the delivery device, and an unlocked configuration, as will be described in greater detail herein. The outer cover member 502 further includes at least a first aperture 510 and a second aperture 512, each defined on an exterior surface on opposing sides of the outer cover member 502, generally adjacent to the proximal end 506. The first and second apertures 510, 512 are configured to receive corresponding first and second protrusions 524, 525 formed on an exterior surface of the the inner cover member 504, as will be described herein.

Additionally, the outer cover member 502 includes a pair of channels or recesses 513 defined along opposing sides of an interior surface of the body of the outer cover member 502 and generally extend an entire length of the outer cover member 502 from the proximal end 506 to the distal end 508 thereof. As will be described herein, the channels 513 are shaped and/or sized to receive a corresponding pair of rails 530 defined along an exterior surface of the inner cover member 504 to thereby allow for sliding movement of the outer cover member 502 relative to the inner cover member 504 when transitioning the cover 500 from the unlocked configuration to the locked configuration.

The inner cover member 504 includes a proximal portion 514 and a distal portion 516, which are generally separated by a hinge member 518. The hinge member 518 is a living hinge, thereby allowing for repeated movement between a closed configuration (as shown when the outer and inner cover members 502, 504 are closed over the needle) and an open configuration (as shown when the outer cover member 502 is transitioned to an unlocked position to expose the needle and the inner cover member 504 is bent back to fully expose the needle for use).

It should be noted that the proximal and distal portions 514, 516 of the inner cover member 504 are further coupled to one another in a breakaway fashion. In particular, the connection 520 between the proximal and distal portions 514, 516 includes perforations, scores, or other cut-outs, thereby allowing for the distal portion 514 of the inner cover member 504 to break away from the proximal portion 514 when a user moves the cover from the closed position to the open position. The connection 520 serves at least two purposes: 1) it is a safety feature in that the perforated or scored connection 520 serves as a breakaway connection, which indicates whether the cover 500 has been used or not and thus whether the needle is safe for use; and 2) it prevents the proximal portion 514 and distal portion 516 from collapsing during manufacture (i.e., the connection 520 helps keep index of the inner cover member 504 throughout its length during the molding process).

Figure 34A:
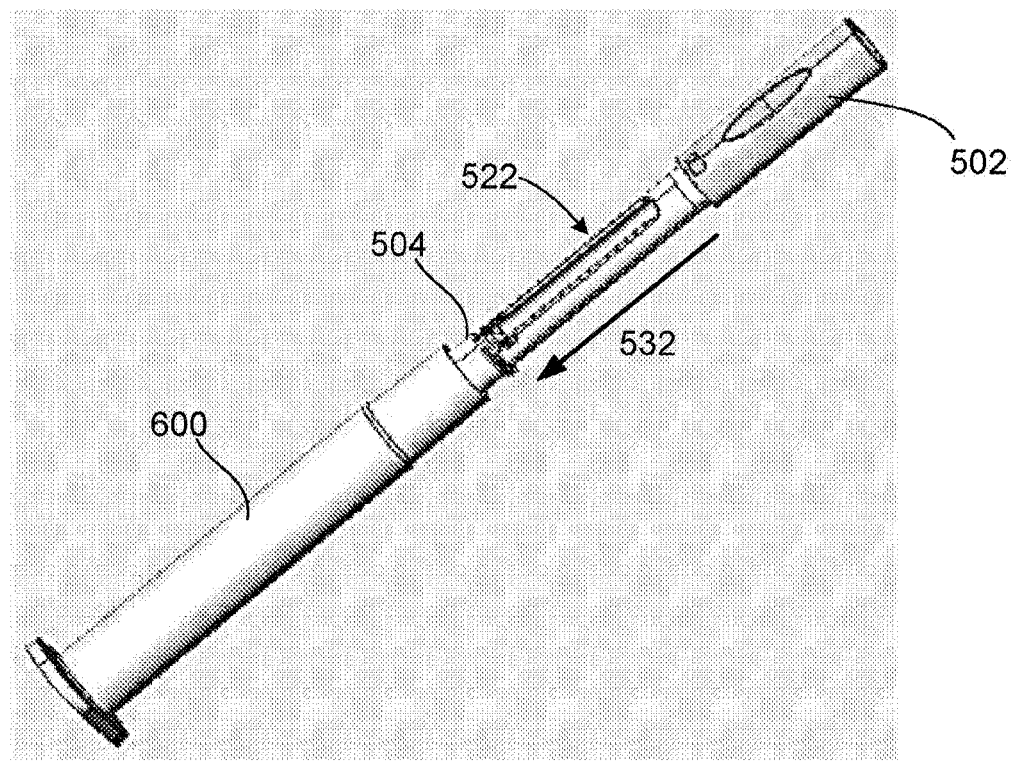
FIG. 34A is a front perspective view of the safety needle cover securely coupled to the hub and in an unlocked configuration, in which the outer cover member is in an unlocked position relative to the inner cover member such that the opening or port of the inner cover member is not blocked or shielded by the outer cover member and the safety needle cover can be opened to expose the needle for delivery of a therapeutic agent.
Figure 34B:
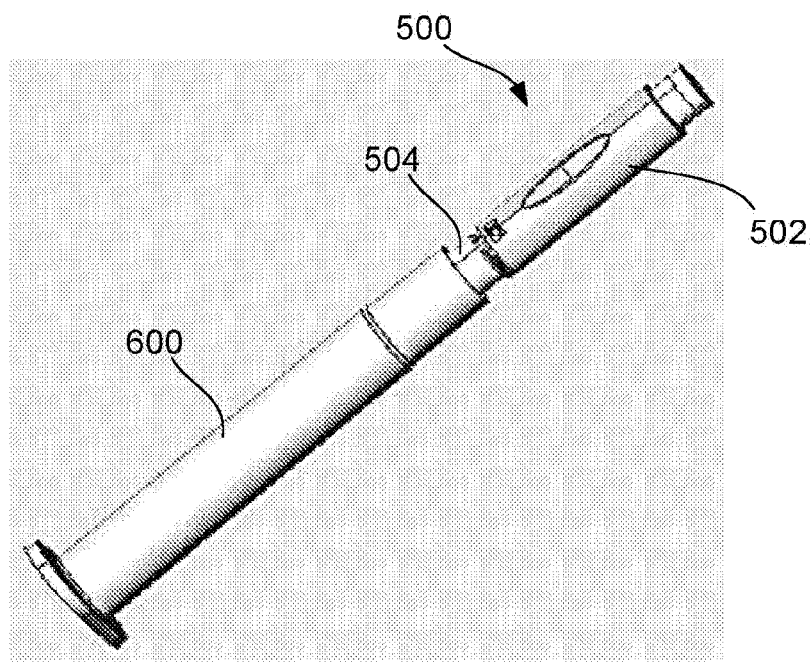
FIG. 34B is a front perspective view of the safety needle cover securely coupled to the hub and in an locked configuration, in which the outer cover member has transitioned from the unlocked position to the locked position relative to the inner cover member such that the outer cover member is covering the opening or port of the inner cover member and thereby preventing access to the needle of the delivery device.

The inner cover member 504 includes an opening or port 522 extending along a length thereof. The opening 522 extends a length from the proximal portion 514 towards the distal portion 516, wherein the length of the opening 522 generally corresponds to a length of the needle extending within the cover members when the cover 500 is coupled to a delivery device with such a needle. Accordingly, when the opening 522 of the inner cover member 504 is not blocked or shield by the outer cover member 502 (i.e., when the outer cover member 502 is in the unlocked position and positioned adjacent to the distal portion 516 of the inner cover member 504, as shown in FIG. 34B), the opening 522 is configured to allow a needle to pass therethrough when the cover 500 bends along the hinge 518. The inner cover member 504 further includes a first protrusion 524 and a second protrusion 525, each extending from an exterior surface on opposing sides of the inner cover member 504, generally closer to the proximal portion 514 than the distal portion 516. The first and second protrusions 524, 525 are configured to be received within and engage the corresponding first and second apertures 510, 512 of the outer cover member 502 to assist in retaining the cover 500 in a locked configuration (i.e., locking the outer and inner cover members 502, 504 to one another thereby preventing access to the needle of the delivery device). The inner cover member 504 may further include a stopping member 519 defined on exterior surface thereof, generally on the proximal portion 514 and adjacent to the hinge member 518. The stopping member 519 may be configured to prevent over extension of the cover when transitioning from the closed position to the open position, in a manner described previously herein with regard to cover 100.

As previously described herein, the first and second protrusions 524, 525 of the inner cover member 504 are configured to be received within the corresponding first and second apertures 510, 512 of the outer cover member 502 when the cover 200 is in the locked configuration. In particular, when a user wants to lock the cover 500, in the event that they have already administered a therapeutic via a needle injection, the user need only slide the outer cover member 502 towards the inner cover member 504 until the first and second protrusions 524, 525 are received within the corresponding first and second apertures 510, 512. At least the first protrusion 524 generally provides a snap-fit engagement when received within the corresponding first aperture 510 such that the outer cover member 502 is difficult and almost impossible to disengage from the inner cover member 504 once moved into the locked position.

Figure 31:
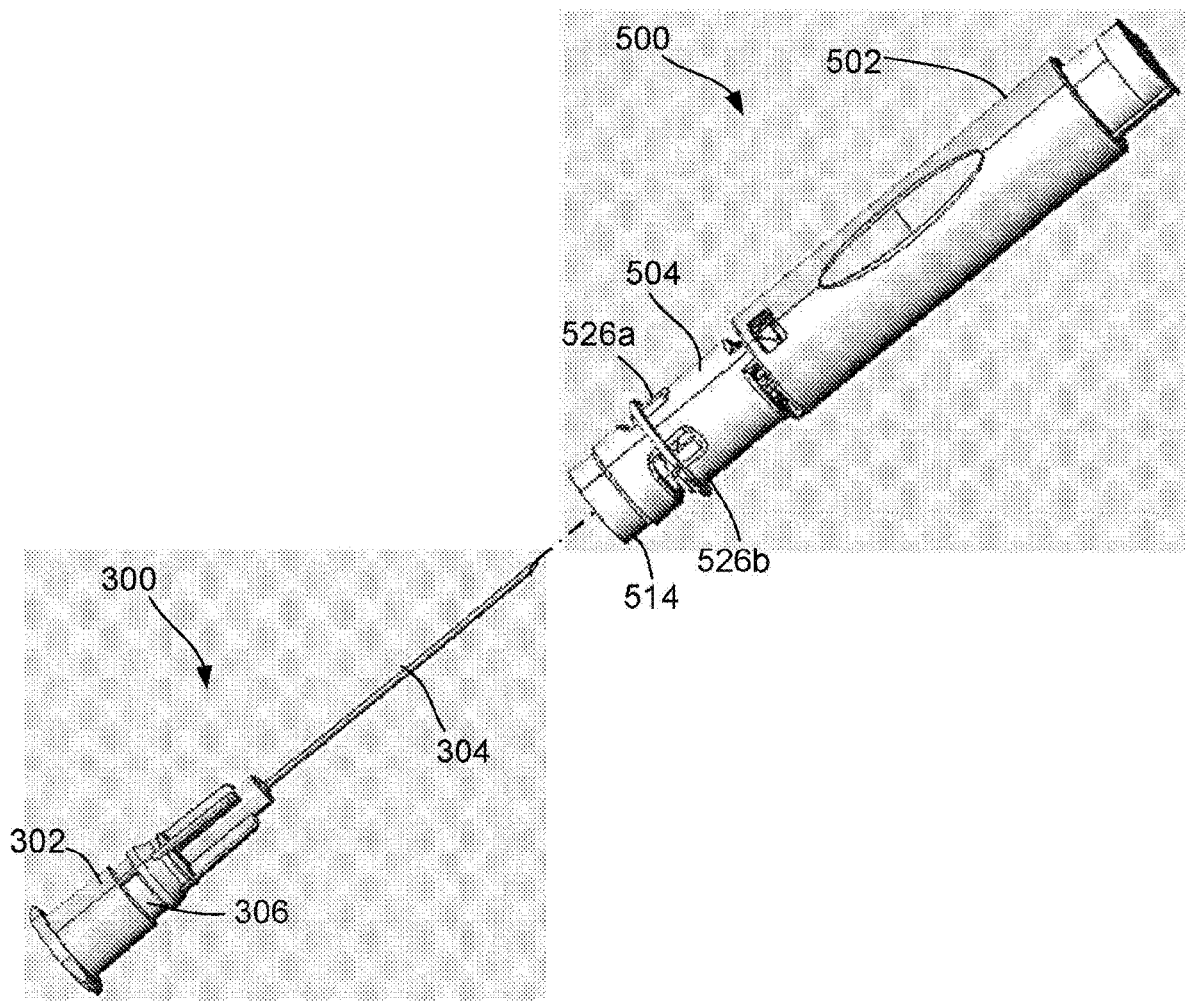
FIG. 31 is a front perspective view of the safety needle cover of FIG. 28 in an assembled configuration and further illustrating the exemplary hub of a delivery device or assembly of FIG. 23 to which the safety needle cover is configured to be directly coupled thereto.

The inner cover member 504 further includes snap-fitting hook members 526a and 526b formed on the proximal portion 514. For example, the snap-fitting hook members 526a and 526b may be positioned on opposing sides of the inner cover member 504, generally opposing one another. Each of the snap-fitting hook members 526a, 526b is configured to engage a corresponding portion of a delivery device to thereby retain the cover 500 to the delivery device, as will be described in greater detail herein. The inner cover member 504 may further include a flange defined along the proximal portion 514 configured to engage a corresponding portion of a handheld tool to be used with the delivery device, such as a syringe barrel or the like (as shown in FIGS. 34A and 34B, for example). FIG. 31 is a front perspective view of the safety needle cover 500, in which the outer and inner cover members 502, 504 are assembled to one another and in a locked configuration, and further illustrating the exemplary hub 300 of a delivery device or assembly (previously described and shown in FIG. 23) to which the safety needle cover 500 is configured to be directly coupled thereto.

As shown, the hub 300 includes a body having a proximal end and a distal end to which a needle 304 is coupled and extending therefrom. The hub 300 may generally resemble a standard ISO-style hub, which includes a standard Luer-Lok fitting at the proximal end and configured to be coupled to a source (e.g., syringe or vial) containing a fluid agent to be delivered, via the needle or other administration means (e.g., nozzle), to a patient. The hub 300 may further include a connection fitting to which the cover 500 may be coupled. For example, as shown, the hub body 302 may have an undercut 306 extending around a perimeter thereof. The cover 500, specifically the inner cover member 504 further includes snap-fitting hook members 526a and 526b formed on the proximal portion 514. For example, the snap-fitting hook members 526a and 526b may be positioned on opposing sides of the inner cover member 504, generally opposing one another. Each of the snap-fitting hook members 526a, 526b is configured to engage the corresponding undercut 306 of the hub 302 upon sliding of the cover 500 onto the hub 300, as shown in FIGS. 32, 33, 34A-34B, and 35A-35B. It should be noted that the hub 300 may also generally resemble non-standard, non-ISO-style hubs which may include non-standard connection fittings.

Figure 33:
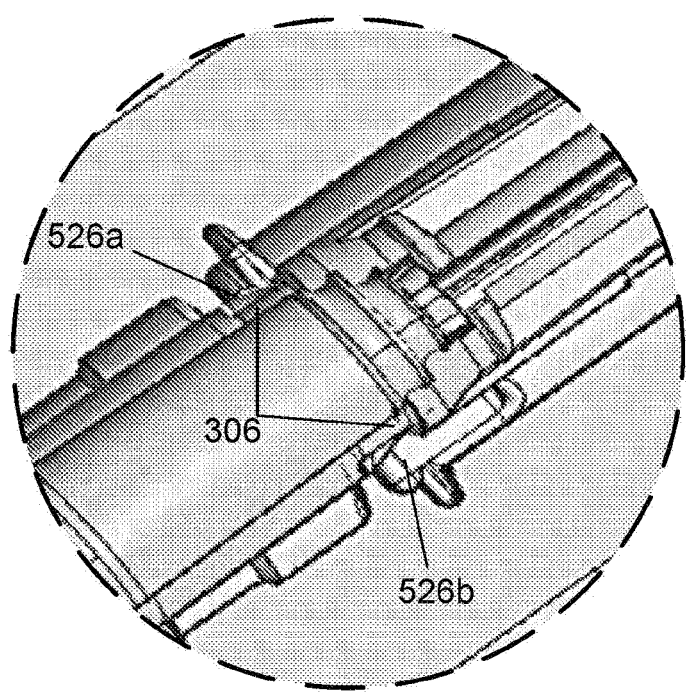
FIG. 33 is an enlarged perspective sectional view of the safety needle cover securely coupled to the hub illustrating engagement between the snap-fitting hook members of the inner cover member engaging corresponding undercuts defined on the body of the hub.

FIG. 32 is a front perspective view of the safety needle cover 500 securely coupled to the hub 300. FIG. 33 is an enlarged perspective sectional view of the safety needle cover 500 securely coupled to the hub 300, illustrating engagement between the snap-fitting hook members 526 of the inner cover member 504 engaging corresponding undercuts 306 defined on the body of the hub 300, as indicated by arrows 400. The engagement between the snap-fitting hook members and the undercut may generally provide a secure engagement between the cover 500 and the hub 300 and make it difficult to remove the cover 500 from the hub 300, thereby increasing safety and preventing unwanted needle stick.

FIG. 34A is a front perspective view of the safety needle cover 500 securely coupled to the hub 300 and in an unlocked configuration, in which the outer cover member 502 is in an unlocked position relative to the inner cover member 504 such that the opening or port 522 of the inner cover member 504 is not blocked or shielded by the outer cover member 502 and the safety needle cover 500 can be opened to expose the needle 304 for delivery of a therapeutic agent.

FIG. 34B is a front perspective view of the safety needle cover 500 securely coupled to the hub 300 and in an locked configuration, in which the outer cover member has transitioned from the unlocked position to the locked position relative to the inner cover member, as indicated by arrow 532, such that the outer cover member is covering the opening or port 522 of the inner cover member 504 and thereby preventing access to the needle 304 of the delivery device.

Figure 34C:
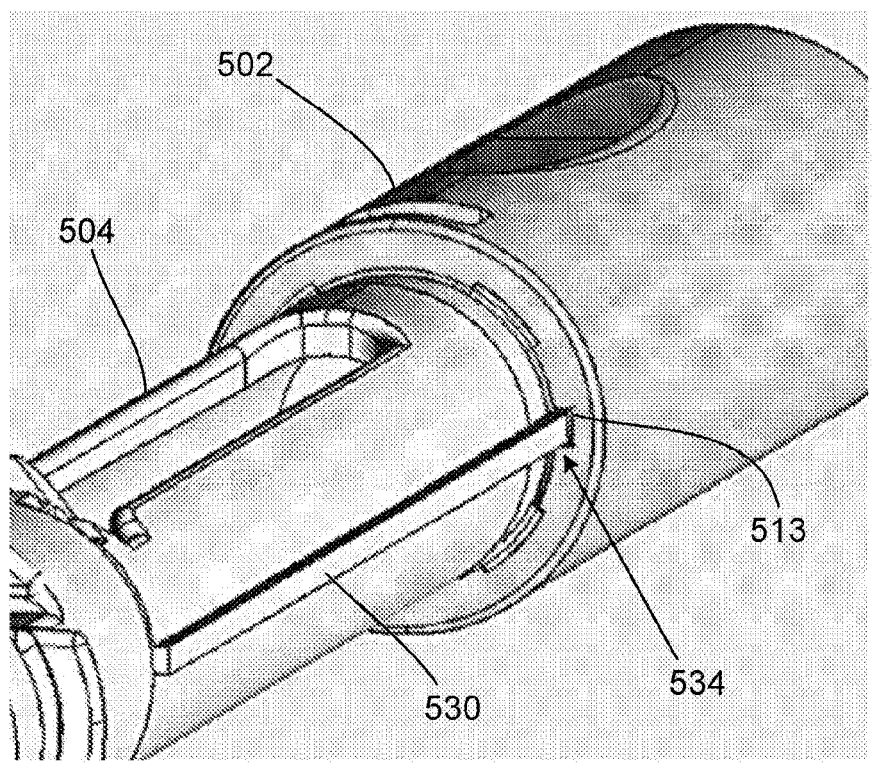
FIG. 34C is an enlarged front perspective view of the safety needle cover in an unlocked configuration, illustrating the cooperative track assembly of the inner and outer cover members allowing the outer cover member to slidably transition between the locked and unlocked configurations.

FIG. 34C is an enlarged front perspective view of the safety needle cover 500 in an unlocked configuration, illustrating the cooperative track-like assembly of the inner and outer cover members 502, 504, consisting of the channels 513 of the outer member 502 receiving the rails 530 of the inner cover member 504, as indicated by arrow 534, thereby allowing the outer cover member 502 to slidably transition from the unlocked position to the locked position relative to the inner cover member 504.

Figure 35A:
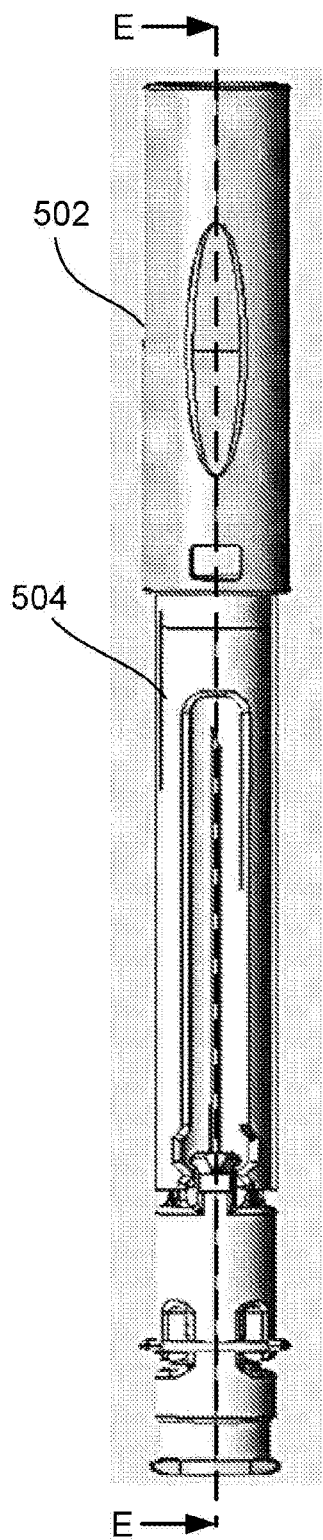
FIG. 35A is front view of the safety needle cover securely coupled to the hub.

FIG. 35A is front view of the safety needle cover 500 securely coupled to the hub and in an unlocked configuration (i.e., the outer and inner cover members 502, 504 are not locked with one another and the opening or port 522 of the inner cover member 504 is exposed).

Figure 35B:
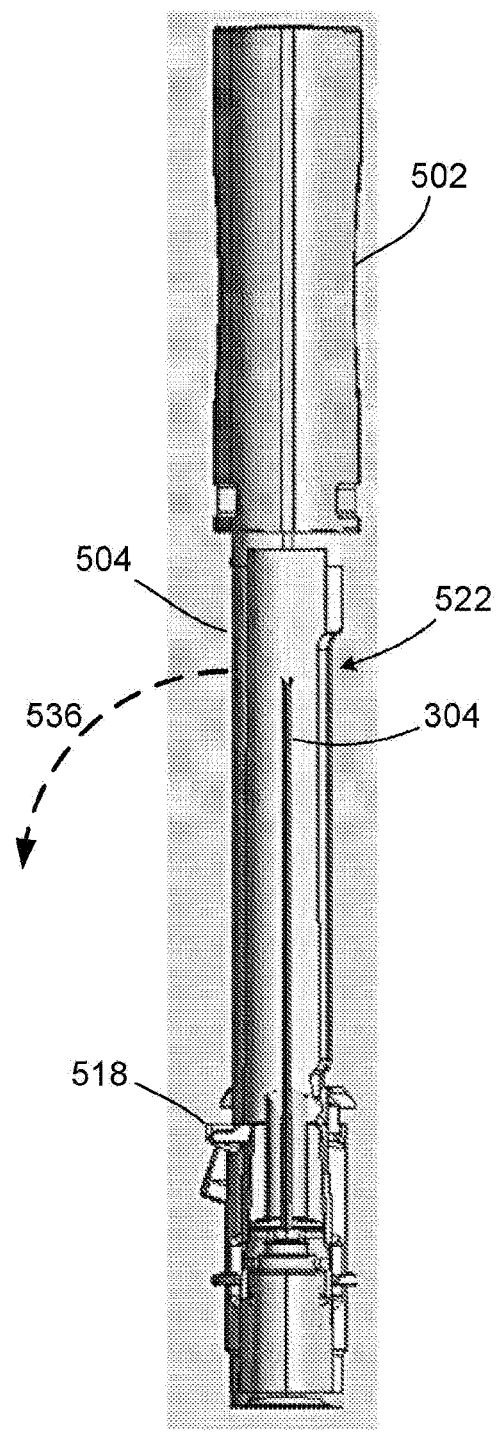
FIG. 35B is an enlarged side sectional view of the safety needle cover securely coupled to the hub taken along lines E-E in FIG. 35A and illustrating engagement between the snap-fitting hook members of the inner cover member engaging corresponding undercuts defined on the body of the hub.

FIG. 35B is an enlarged side sectional view of the safety needle cover securely coupled to the hub taken along lines E-E in FIG. 35A and illustrating engagement between the snap-fitting hook members of the inner cover member engaging corresponding undercuts defined on the body of the hub. When in the unlocked configuration, a user may easily open the cover 500 to expose the needle 304 for use by simply bending the top end or distal end of the cover 500 (including the outer cover member 502 and the distal portion 516 of the inner cover member 504) in a direction indicated by arrow 536. Upon sufficient application of force, the connection 520 between the proximal and distal portions 514, 516 will start to fail, thereby allowing for the distal portion 516 of the inner cover member 504 to break away from the proximal portion 514 when a user moves the cover from the closed position to the open position. Upon using the needle (i.e., administering an injection or the like), the user need only bend the distal end of the cover 500 back to a closed position and then simply slide the outer cover member 502 towards the inner cover member 504 until the outer and inner cover members 502, 504 are locked into engagement with one another (i.e., the protrusions 524, 525 of the inner cover member 504 engage the corresponding apertures 510, 512 of the outer cover member 502). While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A safety cover configured to be coupled to an injection device and to provide a protective enclosure for a needle of the injection device, the safety cover comprising:

an outer cover member;
an inner cover member coupled to the outer cover member in a coaxial arrangement so that the outer cover member encloses at least a portion of the inner cover member,
wherein the outer cover member is configured to move relative to the inner cover member from an unlocked position, in which the needle of the injection device is accessible for use, to a locked position, in which the outer cover member and the inner cover member are fixed at one another and the needle of the injection device is inaccessible for use,
wherein the outer cover member includes a body that includes a proximal end, a distal end, and a cavity defined within the body,
wherein the cavity is shaped and sized to receive a least a portion of the inner cover member,
wherein the outer cover member includes at least one first recess or aperture defined on a portion of the outer cover member axially offset in its entirety from a tip of the needle in a direction distal from the tip of the needle in the locked position and in the unlocked position of the outer cover member, and
wherein the inner cover member includes a body that includes a proximal end and a distal end coupled to one another by a hinge member,
wherein an axial cavity extending from the proximal end of the inner cover member supports the injection device including a hub that supports the needle,
wherein the body of the inner cover member including the proximal end, the distal end, the axial cavity and the hinge member are integrally provided in one piece by injection molding,
wherein the inner cover member includes a cavity that is defined within the inner cover member and that is shaped and sized to enclose the needle of the injection device within the cavity when the safety cover is coupled to the injection device,
wherein the inner cover member includes at least one first radial protrusion that extends from an exterior surface of the inner cover member and that is configured to engage the at least one first recess or aperture of the outer cover member when the outer cover member is in the locked position to prevent movement of the outer cover member,
wherein the inner cover member is arrangeable in a closed position, in which the proximal end and distal end are aligned with one another along a common plane and share a common longitudinal axis, and in an open position, in which the distal end is bent, via the hinge member, out of the common plane relative to the proximal end to expose the needle for use when the outer cover member is in the unlocked position,
wherein the outer cover member and the inner cover member are rotatably coupled to one another so that the outer cover member is configured to rotate relative to the inner cover member from the unlocked position to the locked position while remaining coupled thereto,
wherein the inner cover member includes a pin having a maximum outer diameter smaller than the distal end of the inner cover member and extending from the distal end of the inner cover member through a corresponding bore in the distal end of the outer cover member,
wherein the pin is received and axially retained within the corresponding bore defined in the distal end of the outer cover member by direct form locking contact between an axial surface of the pin and an external axial surface of the distal end of the outer cover member,
wherein the outer cover member is configured to rotate relative to the inner cover member about a longitudinal axis of the pin.

2. The safety cover of claim 1, wherein the inner cover member includes an opening or port extending along a length thereof from the proximal end towards the distal end, wherein the length of the opening or port corresponds to a length of the needle extending within the inner cover member.

3. The safety cover of claim 2,
wherein the outer cover member includes an opening or port extending along a length thereof from the proximal end towards the distal end, and
wherein the length of the opening or port generally corresponds to a length of the needle extending within the inner cover member.

4. The safety cover of claim 3, wherein the outer cover member includes a tab member positioned relative to the opening or port and coupled thereto via a breakaway connective member including a plurality of perforations or scores or cut-outs to allow for the tab member to be torn from the outer cover member to fully expose the opening or port.

5. The safety cover of claim 3, wherein the openings or ports of the inner cover member and outer cover member have corresponding shapes and lengths.

6. The safety cover of claim 5,
wherein the openings or ports of the inner cover member and the outer cover member are aligned with one another in the unlocked position to allow the inner cover member to transition from the closed position to the open position to fully expose the needle for use.

7. The safety cover of claim 5, wherein the openings or ports of the inner cover member and the outer cover member are misaligned with one another in the locked position to prevent the inner cover member from transitioning from the closed position to the open position.

8. The safety cover of claim 1, wherein the outer cover member and the inner cover member are slidably coupled to one another so that the outer cover member is configured to slide relative to the inner cover member from the unlocked position to the locked position while remaining coupled thereto.

9. The safety cover of claim 1, wherein the hinge member includes a shape memory characteristic.

10. The safety cover of claim 9, wherein the hinge member has a default state and is configured to return to the default state upon release of application of force upon the distal end of the inner cover member.

11. The safety cover of claim 10, wherein the default state is associated with the inner cover member in the closed position.

12. The safety cover of claim 1, wherein the proximal end and the distal end of the inner cover member are coupled to one another via a breakaway connective member.

13. The safety cover of claim 12, wherein the breakaway connective member includes a plurality of perforations or scores or cut-outs configured to allow for the proximal end and the distal end of the inner cover member to break away from one another upon sufficient application of force upon the distal end when initially transitioning from the closed position to the open position.

14. The safety cover of claim 1,
wherein the at least one first protrusion of the inner cover member includes a biasing member for applying a biasing force in an outward direction, thereby securely engaging the at least one first protrusion within a first aperture and preventing disengagement therefrom when the outer cover member is in the locked position.

15. The safety cover of claim 1,
wherein the inner cover member incudes at least one pair of snap-fitting hook members formed on the proximal end and defined on opposing sides thereof and opposing one another, and
wherein each snap-fitting hook member of the at least one pair of snap-fitting hook members is configured to engage a corresponding portion of the injection device to retain the safety cover on the injection device.

16. The safety cover according to claim 1,
wherein the distal end of the outer cover member includes a flat handle that extends axially from the outer cover member beyond the pin and that includes a cutout that envelops the pin with a clearance so that the pin is radially accessible from an outside of the outer cover member.

* * * * *